(12) United States Patent  (10) Patent No.: US 8,197,061 B2
Kindl  (45) Date of Patent: Jun. 12, 2012

(54) EAR SHADES

(76) Inventor: Daniel J. Kindl, Broadview Heights, OH (US)

( * ) Notice: Subject to any disclaimer, the term of this patent is extended or adjusted under 35 U.S.C. 154(b) by 0 days.

(21) Appl. No.: 12/999,665

(22) PCT Filed: Jun. 17, 2009

(86) PCT No.: PCT/US2009/047615
§ 371 (c)(1),
(2), (4) Date: Apr. 18, 2011

(87) PCT Pub. No.: WO2009/155320
PCT Pub. Date: Dec. 23, 2009

(65) Prior Publication Data
US 2011/0187988 A1    Aug. 4, 2011

Related U.S. Application Data

(60) Provisional application No. 61/073,890, filed on Jun. 19, 2008.

(51) Int. Cl.
*G02C 5/14* (2006.01)
(52) U.S. Cl. ............................... 351/123; 2/209
(58) Field of Classification Search .................. 351/123, 351/122, 111, 41; 2/209, 174, 423, 449, 2/422; D16/339, 338, 330
See application file for complete search history.

(56) References Cited

U.S. PATENT DOCUMENTS

| | | | |
|---|---|---|---|
| 538,151 A | 4/1895 | Bussey | |
| 830,439 A | 9/1906 | James | |
| 915,757 A | 3/1909 | Fay | |
| 1,048,191 A | 12/1912 | Maurice | |
| 1,117,968 A | 11/1914 | Bobory | |
| 1,468,556 A | 9/1923 | Camp et al. | |
| 1,471,967 A | 10/1923 | Mahlmann | |
| 1,619,772 A | 3/1927 | Thompson | |
| 1,706,682 A | 3/1929 | Takacs | |
| 1,759,041 A | 5/1930 | Dawes | |
| 3,533,687 A | 10/1970 | Herzig | |

(Continued)

FOREIGN PATENT DOCUMENTS

GB          694748          7/1953

OTHER PUBLICATIONS

International Search Report dated Jul. 23, 2009, for International Application No. PCT/US2009/047615.

(Continued)

*Primary Examiner* — Hung Dang
(74) *Attorney, Agent, or Firm* — Calfee, Halter & Griswold LLP

(57) ABSTRACT

The present invention relates to a device used to protect the ears from the sun Exemplary embodiments of the invention include ear shades for use with a pair of glasses The temple arm of the glasses generally comprises an anterior end, a posterior end, an ear support portion, and a shading portion The anterior end of the temple arm may be configured to be operatively connected to a lens holding portion of the glasses and the ear support portion rests on the ear The shading portion may be operatively connected to the ear support portion and cooperates with the ear support portion to create a downward-opening cavity into which the top of the user's ear extends to shade at least the top of the user's ear.

20 Claims, 24 Drawing Sheets

U.S. PATENT DOCUMENTS

| | | |
|---|---|---|
| 3,684,356 A | 8/1972 | Bates |
| 4,670,911 A | 6/1987 | Dunford |
| D290,964 S | 7/1987 | Kalbach |
| 4,682,374 A | 7/1987 | Geiser |
| 4,751,746 A | 6/1988 | Rustin |
| 4,802,245 A | 2/1989 | Miano |
| 4,856,089 A | 8/1989 | Horton |
| 5,092,667 A | 3/1992 | Bagley |
| 5,119,514 A | 6/1992 | Woehl |
| D331,130 S | 11/1992 | Williams |
| 5,201,856 A | 4/1993 | Edwards |
| 5,323,493 A * | 6/1994 | Ogiba ............... 2/422 |
| 5,351,343 A | 10/1994 | Harbison |
| 5,402,189 A | 3/1995 | Gill |
| 5,416,923 A | 5/1995 | Peugh |
| 5,440,355 A | 8/1995 | Ross |
| 5,493,733 A | 2/1996 | Pospisil |
| D371,150 S | 6/1996 | Bolash, IV |
| 5,619,750 A | 4/1997 | Allewalt |
| 5,666,664 A | 9/1997 | Hamilton |
| D384,968 S | 10/1997 | Scroy |
| 5,673,438 A | 10/1997 | Lambert |
| D388,115 S | 12/1997 | Celaschi et al. |
| 5,718,002 A | 2/1998 | Pavlak |
| 5,850,637 A * | 12/1998 | Lewis ............... 2/455 |
| 5,877,837 A | 3/1999 | Hayes |
| 5,943,703 A | 8/1999 | Avila, Jr. |
| 6,029,282 A | 2/2000 | Buschman |
| 6,041,440 A | 3/2000 | Jackson |
| 6,065,157 A * | 5/2000 | Felman ............... 2/209 |
| 6,067,664 A | 5/2000 | Cortes |
| 6,278,788 B1 | 8/2001 | Landis et al. |
| D449,640 S | 10/2001 | Grundy |
| 6,550,064 B2 | 4/2003 | Schmitt et al. |
| 6,860,598 B1 | 3/2005 | Bigda |
| 7,020,901 B2 | 4/2006 | Brhel |
| 7,117,546 B2 | 10/2006 | Goulding |
| 7,134,147 B2 * | 11/2006 | Yount ............... 2/209 |
| 2001/0029622 A1 | 10/2001 | Bose et al. |
| 2002/0010452 A1 | 1/2002 | Dupuy |
| 2002/0170106 A1 | 11/2002 | Ducker Lebherz |
| 2003/0229932 A1 | 12/2003 | Whelan et al. |
| 2005/0015852 A1 | 1/2005 | Brhel |

OTHER PUBLICATIONS

Written Opinion dated Jul. 23, 2009, for International Application No. PCT/US2009/047615.

International Preliminary Report on Patentability dated Dec. 21, 2010, for International Application No. PCT/US2009/047615.

\* cited by examiner

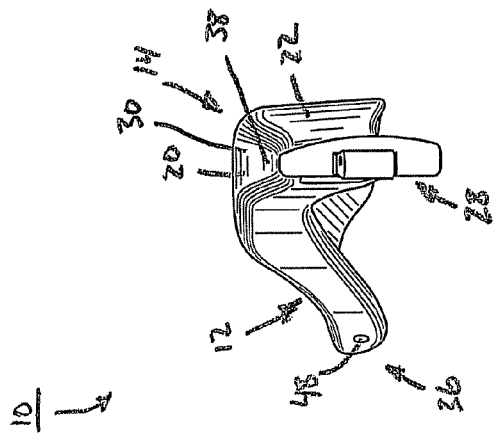
FIG. 3
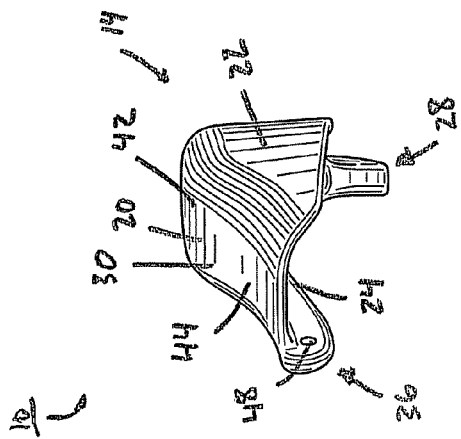
FIG. 4
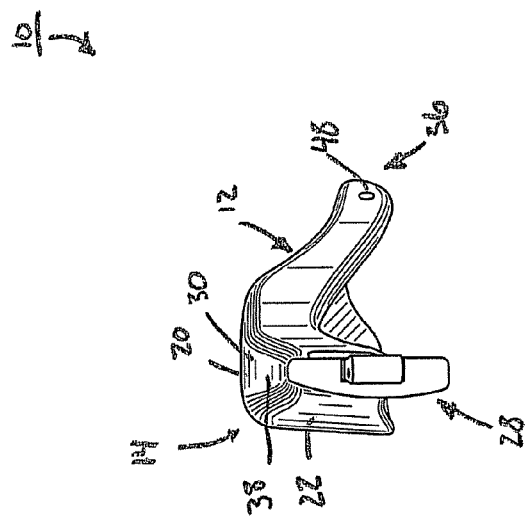
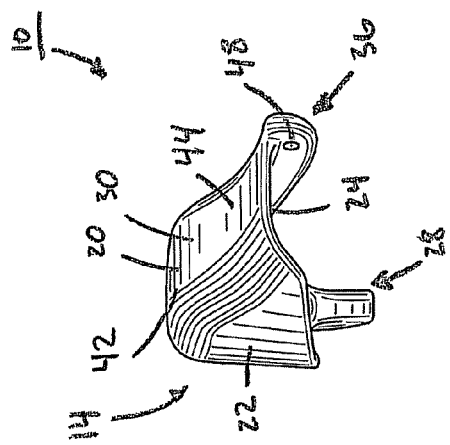

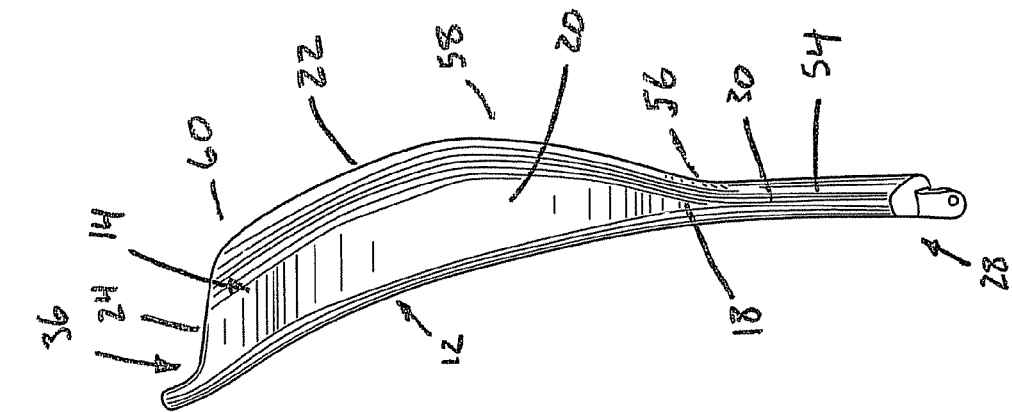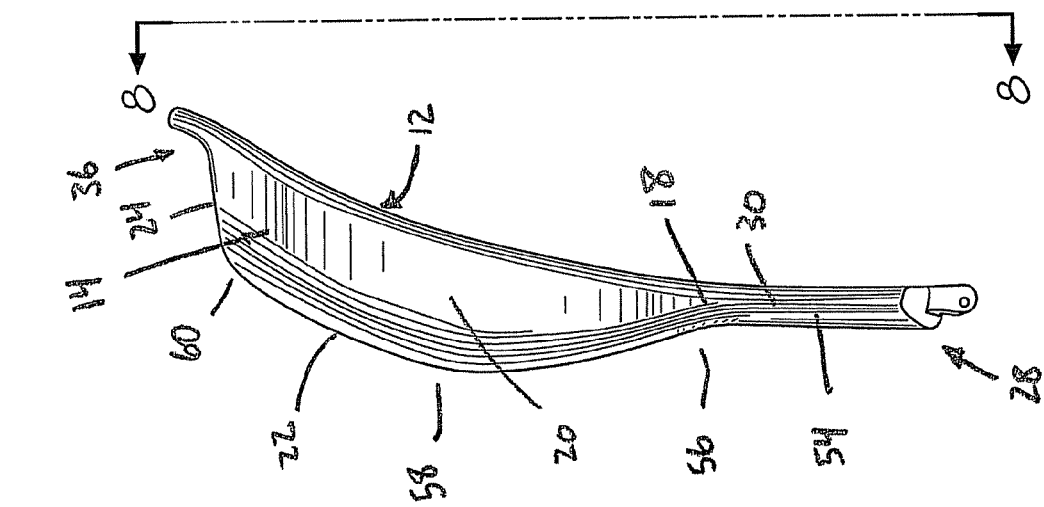
FIG.5

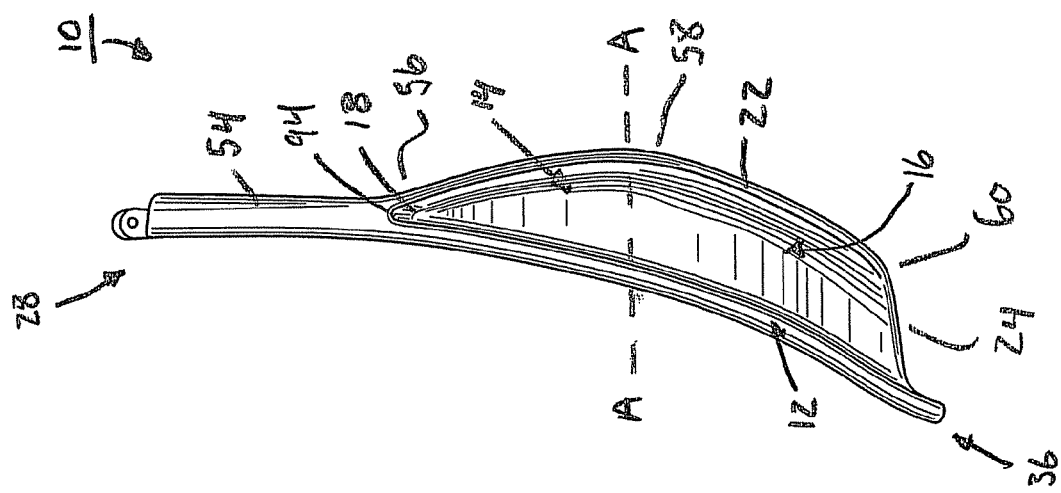
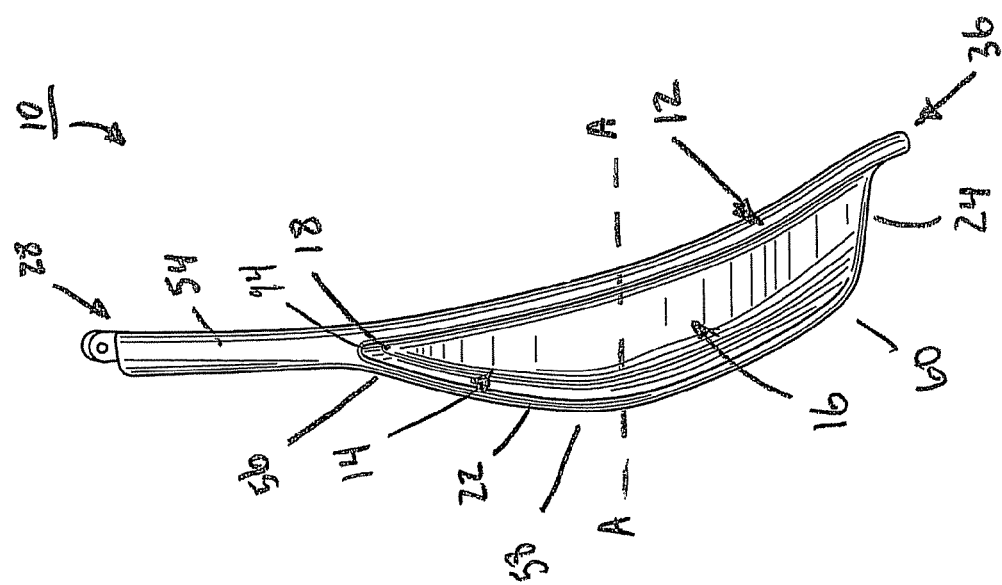
FIG. 6

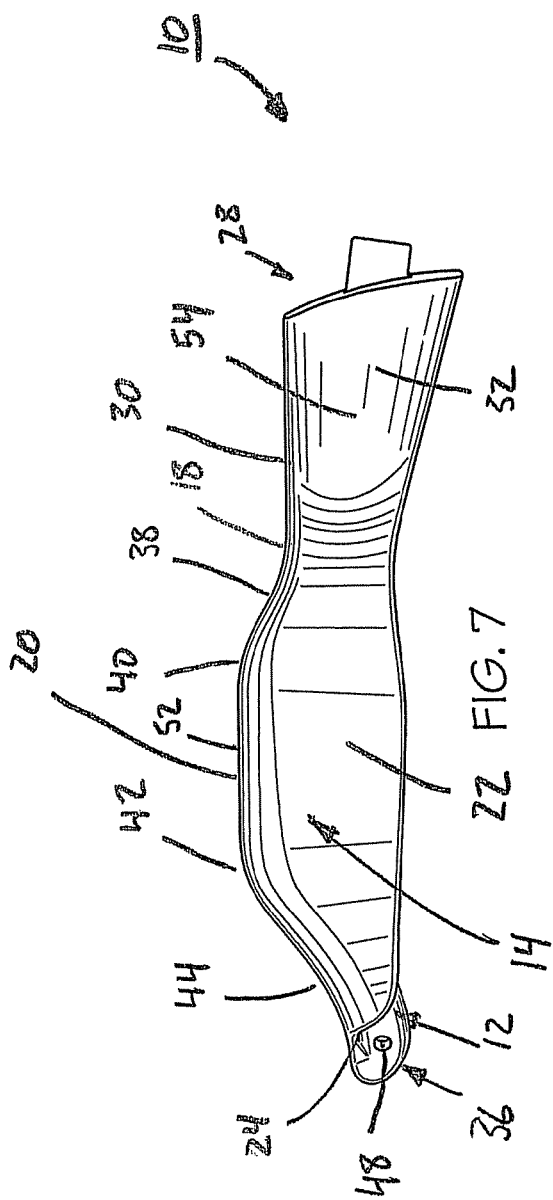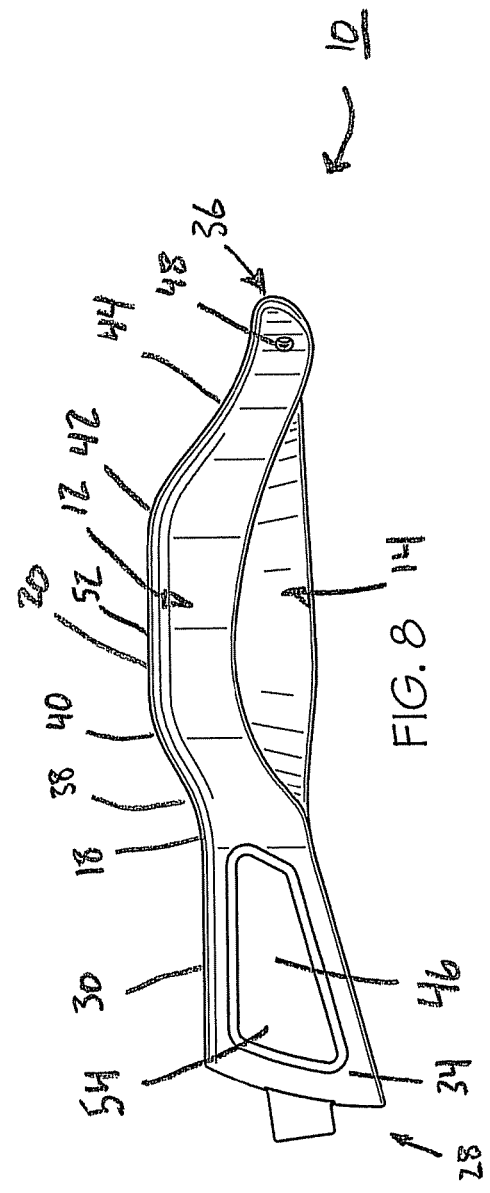

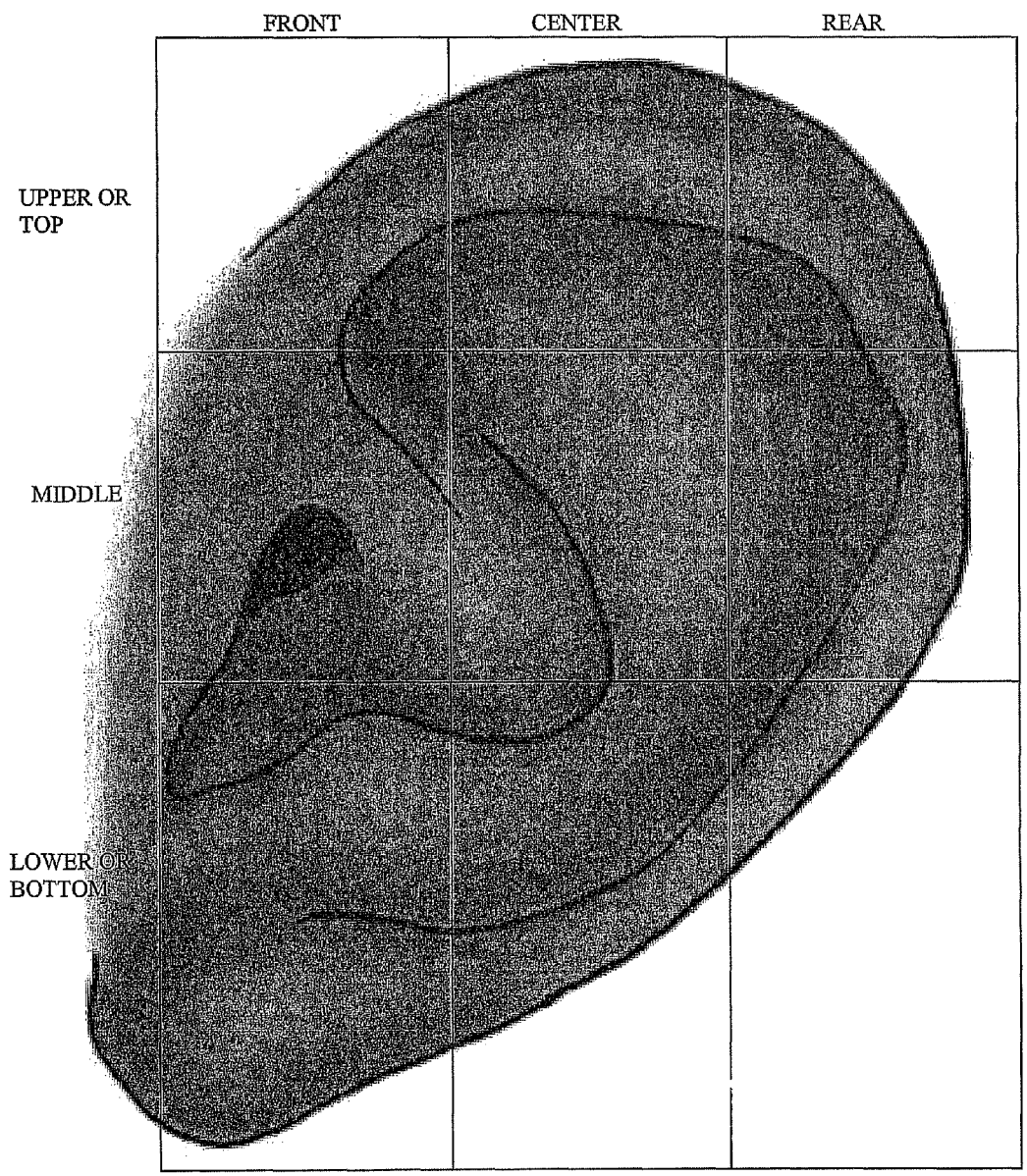
FIG. 10A - EAR PORTIONS

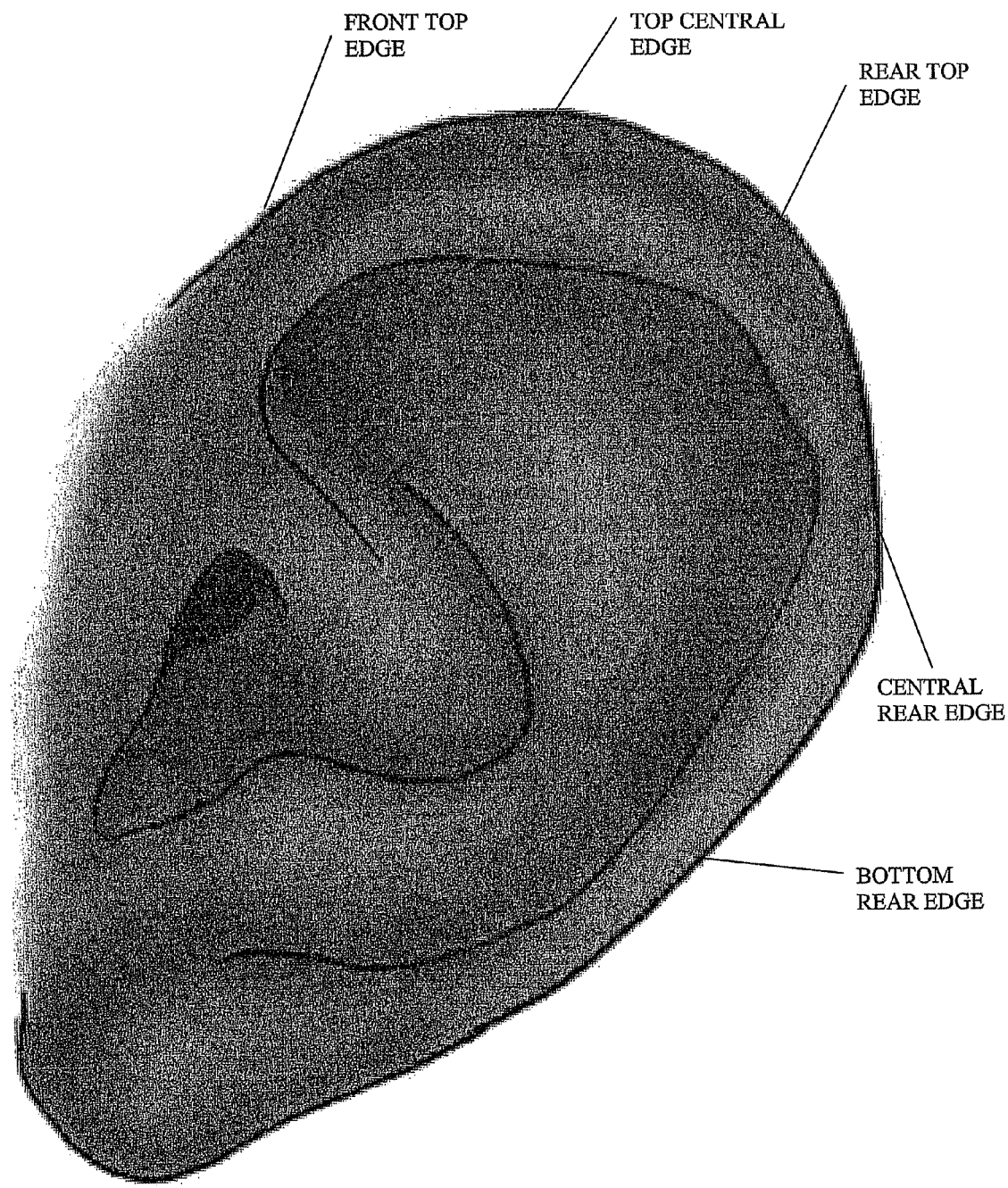
FIG. 10B - EAR EDGES

FIG. 11A

EAR SHADES

RELATED APPLICATION

The present application is a national phase entry under 35 U.S.C. §371 and claims priority to International Application No. PCT/US2009/047615, with an International Filing Date of Jun. 17, 2009, itself claiming priority to, and any other benefit, of U.S. Provisional Patent Application Ser. No. 61/073,890, filed Jun. 19, 2008, and entitled EAR SHADES, the entire contents of which are both hereby incorporated by reference.

TECHNICAL FIELD

The present invention relates to a device used to protect the ears from the sun. Exemplary embodiments of the invention include ear shades for use with a pair of glasses.

BACKGROUND

Sunlight produces ultraviolet (UV) radiation that can directly damage the cells of the skin resulting in skin cancer. People who are frequently outdoors (e.g., farmers, gardeners, construction workers, boaters, golfers, etc.) are at the highest risk of developing skin cancer. Skin cancer often develops on the top of the ear because of its direct exposure to the sun's harmful UV rays. To protect the ear from the sun, people often wear wide brimmed hats that cover the ears and/or sunscreen. However, the option of wearing sunscreen or a wide brimmed hat is often not possible or desired in connection with various activities, or perhaps unavailable.

SUMMARY

Ear shades are provided that shade at least a top portion of the user's ears from the sun. The shades may be open or closed in the front (anterior) and/or open or closed at the rear (posterior).

Exemplary embodiments of the invention include temple arms for glasses that when worn by a user are capable of shading at least a top portion of the user's ears from the sun. The temple arm generally comprises an anterior end, a posterior end, an ear support portion, and a shading portion. The anterior end of the temple arm may be configured to be operatively connected to a lens holding portion of the glasses and the ear support portion rests on the ear. The shading portion may be operatively connected to the ear support portion and may cooperate with the ear support portion to create a downward-opening cavity into which the top of the user's ear extends to shade at least the top of the user's ear. The downward-opening cavity may be formed by at least a closed front portion for shading a top front edge of the user's ear and a top portion for shading a top central edge of the user's ear. The downward-opening cavity may have an open back at the posterior end of the temple arm. The open back of the downward-opening cavity permits the temple arm to be pulled forward without catching on the ear when a user removes the glasses.

Additional and/or alternative advantages, objects, and/or salient features of the invention will become apparent from the following detailed description, which, taken in conjunction with the annexed drawings and claims, disclose preferred embodiments of the invention.

BRIEF DESCRIPTION OF THE DRAWINGS

FIG. 3 is a front elevational view thereof;

FIG. 4 is a rear elevational view thereof;

FIG. 5 is a top plan view thereof;

FIG. 6 is a bottom plan view thereof;

FIG. 7 is a right side elevational view thereof for which the left side elevational view would be a mirror image of FIG. 7;

FIG. 8 is an inside view thereof viewed along 8-8 in FIG. 5;

FIGS. 10A and 10B are schematic representations of a human ear, showing various parts of the ear referred to herein;

FIGS. 11A-11B show other exemplary embodiments having air vents; and

FIGS. 12A-12M are photographs showing various views of an exemplary implementation of the exemplary embodiment of FIGS. 1-9 on a sheet of ¼ inch (i.e., 4 blocks=1 inch) grid paper.

DETAILED DESCRIPTION

Figure 1:
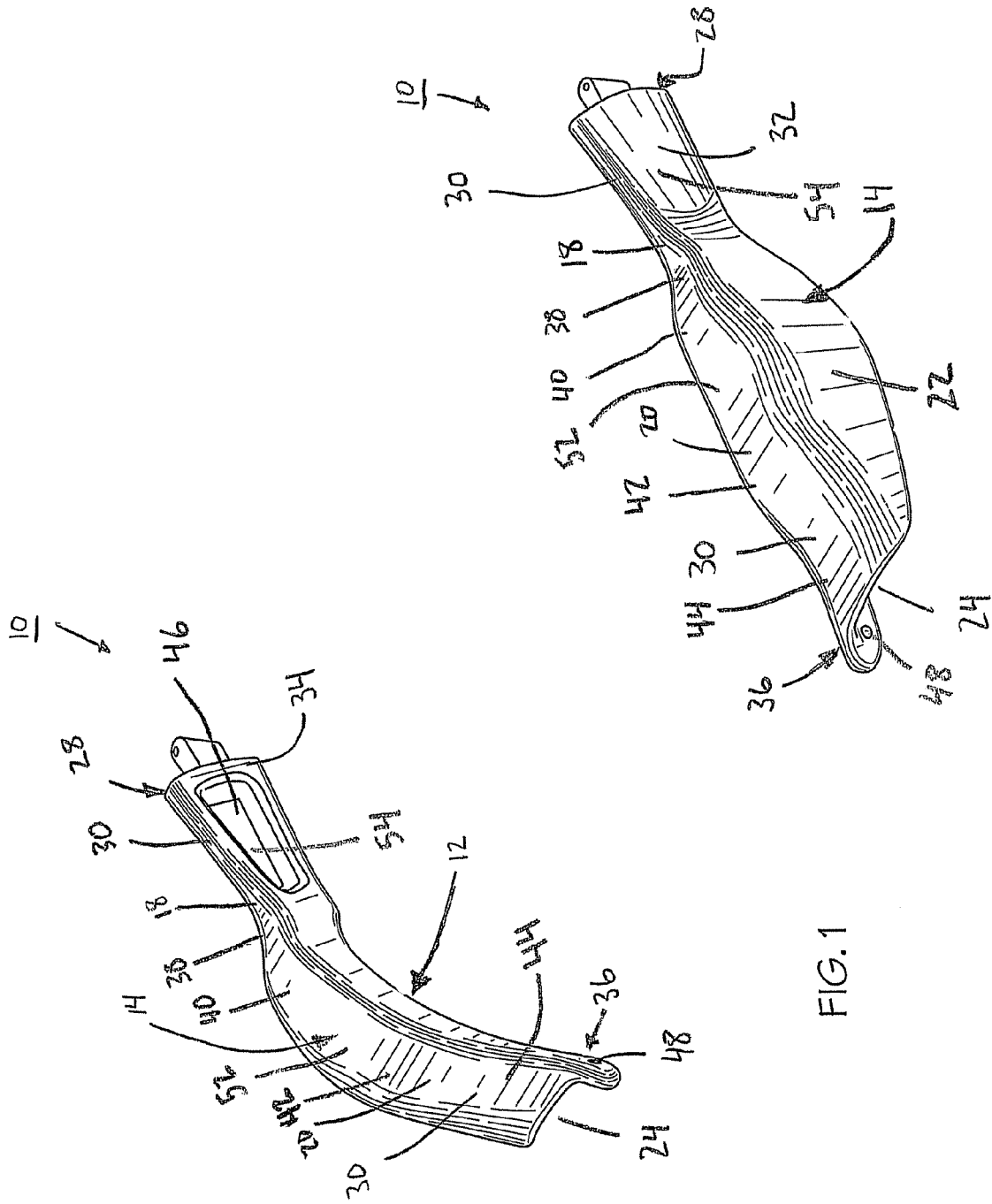
FIG. 1 is a rear/right/top perspective view of a pair of ear shades according to an exemplary embodiment of the invention.
Figure 2:
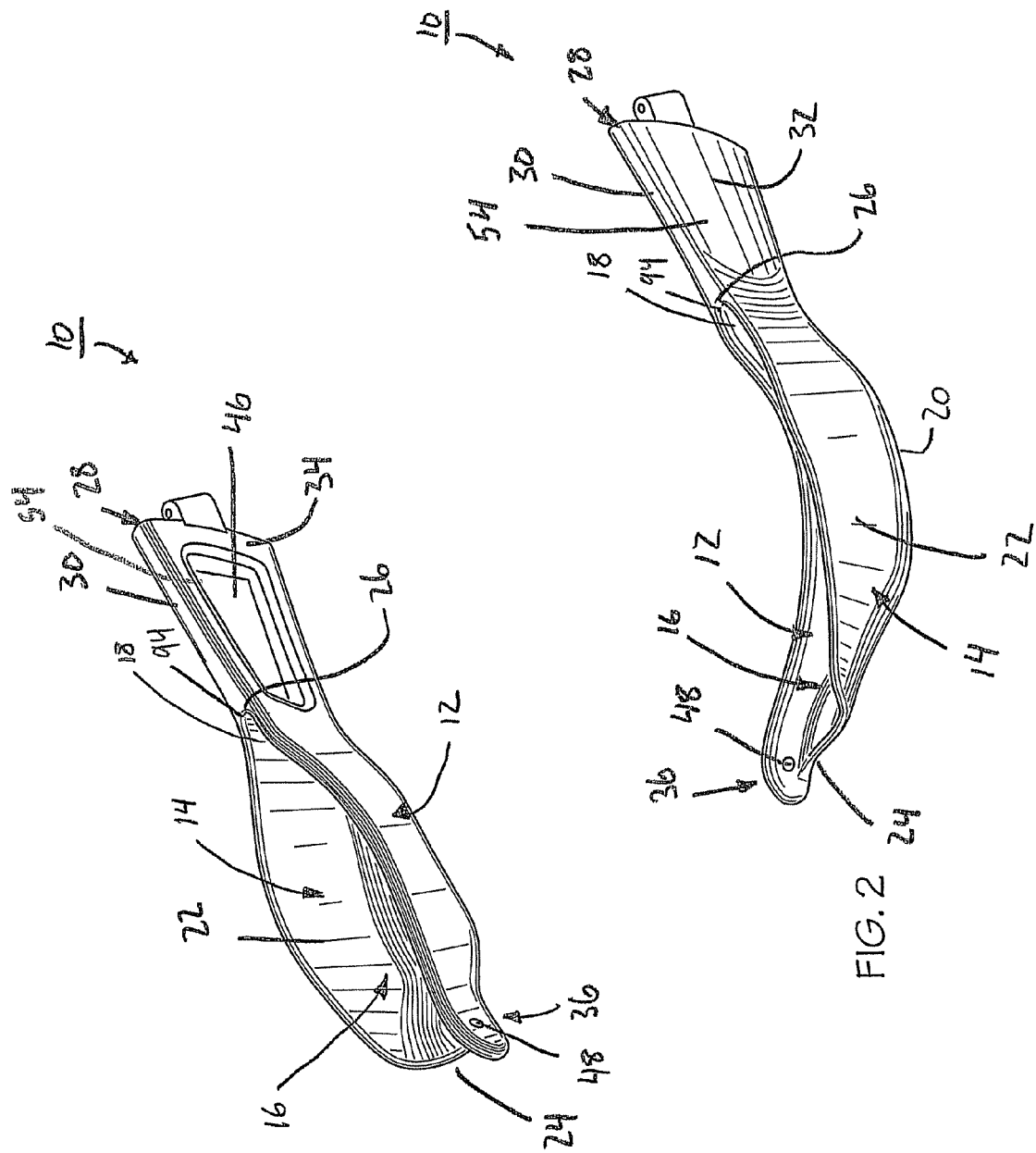
FIG. 2 is a rear/left/bottom perspective view thereof.

This Detailed Description merely describes exemplary embodiments of the invention and is not intended to limit the scope of the specification in any way. Indeed, the invention as described is broader than and unlimited by the preferred embodiments, and the terms used have their full ordinary meaning.

Exemplary embodiments of the invention include a temple arm for glasses that when worn by a user are capable of shading at least a top portion of the user's ear from the sun. The temple arm generally comprises an anterior end, a posterior end, an ear support portion, and a shading portion. The anterior end of the temple arm may be configured to be operatively connected to a lens holding portion of the glasses and the ear support portion rests on the ear. The lens holding portion may comprise any suitable material known in the art, such as for example, plastic (e.g., polycarbonate or acetate), metal, or wood. Further, the lenses may block about 100% of UV rays, including A, B, and C wavelengths. The anterior end may be operatively connected to the lens holding portion by any suitable method known in the art, such as for example, a pin, a screw, a hinge, or other fastener. The temple arm may also be integrally formed with the lens holding portion of the glasses, such as with a living hinge. The anterior end of the temple arm may be any suitable width known in the art. Further, the temple arm may be used with any suitable size and style of glasses or lens holding portion known in the art.

The shading portion of the temple arm may be operatively connected to the ear support portion and cooperates with the ear support portion to create a downward-opening cavity into which the entire top of the user's ear extends to shade at least the top of the user's ear. The downward-opening cavity may be formed by at least a closed front portion for shading a top front edge of the user's ear and a top portion for shading a top central edge of the user's ear. The downward-opening cavity may have an open back at the posterior end of the temple arm. The open back of the downward-opening cavity permits the temple arm to be pulled forward without catching on the ear when a user removes the glasses. Further, at least part of the outer surface of the shading portion or ear support portion may extend rearward, or posteriorly, and perhaps upward, at various lengths relative to other portions of the temple arm or the shade. These extensions may include or comprise expressive elements, such as "fins" (e.g., those fins that adorned various automobiles) or tail pipes, etc.

As stated, the ear support portion rests on the ear to support the glasses. In exemplary embodiments, the shading portion of the device is not intended to rest on the top of the ear, and the outside of the shade portion is not intended to touch the side of the ear. Accordingly, there will ordinarily air gaps between the shade portion and the top and side of the ear. For some users however, e.g., users with larger ears, the top of the ear may contact the shading portion of the device. Accordingly, all the embodiments of the invention may optionally include on one or more inner surfaces of the shading portion some material to cushion the user's ear against the shade portion and/or thermally insulate the user's ear from the shading portion, which might become warm in the sun. Any suitable cushioning and/or thermally insulating material may be used. Foam or rubber may be used as a cushion, and may also provide thermal insulation. Whatever material is used, the material may by attached to the shade portion of the device using, for example, an adhesive or fastener(s), or integrally molded with the shading portion of the device. Further, the material, or spacer, may be separate and held by friction, or pinched, within a downward-opening cavity of the shade portion. The material may be attached to the shade portion prior to sale, or provided as a kit with instructions to couple the material in the shade, e.g., with adhesive or fastener(s) or by friction.

Exemplary embodiments may shade a particular percentage, e.g., at least 20% or 25% or 30% or 40% or 50% of the ear from sunlight coming from directly above, and from directly in front of the wearer. The temple arm may shade at least an upper front portion, an upper center portion, an upper rear portion, a middle front portion, a middle center portion, a middle rear portion, and a lower rear portion of the ear. In some embodiments, at least part of the shading portion helps prohibit wind burn on portions of the ear. For example, the embodiments that are closed in the front and form a pocket into which the ear is inserted help prevent wind burn at the front top edge of the wearer's ear and along the top thereof.

Exemplary embodiments of the invention may include a temple arm comprising an anterior end, a posterior end, a temple bar, a top shade portion, an outside shade portion, and an ear support portion. The anterior end of the temple arm may be configured to be operatively connected to a lens holding portion of the glasses. The temple bar may be located at the anterior end of the temple arm. The top shade portion and the outside shade portion cooperate together to shade at least the top central edge of the user's ear and the rear top edge of the user's ear. The outside shade portion extends downward from the top shade portion to shade at least the top central portion of the user's ear and the top rear portion of the user's ear. The top shade portion further comprises a downward-facing concave surface transitioning to a downward-facing convex surface at the posterior end of the top shade portion to facilitate removal of the glasses by pulling forward. The top shade portion and the outside shade portion are sized and configured to leave the bottom rear edge of the user's ear and the entire lower portion of the user's ear uncovered. The ear support portion extends downward from the top shade portion to form an ear support to support the glasses on the user's ear.

The temple arm may comprise any suitable material known in the art, such as for example, plastic (e.g., polycarbonate or acetate), metal, or wood. Further, the temple arm may comprise a unitary piece of material, such as a single molded piece. As such, the shading portion and the remainder of the temple arm may have a unibody, or unbuilt, construction and provide the dual function of shading the ear and supporting, or holding, the glasses on the ear of the user. In some embodiments, the cavity of the temple arm is overmolded over a piece configured to be operatively connected to the lens holding portion of the glasses.

Referring now to the figures, an exemplary embodiment of the present invention is shown in FIGS. 1-9. It should be noted that the present invention is not presently intended to be limited to the specific spacing shown in the Figures between the exemplary pair of ear shades and/or the angle between the longitudinal axis of the exemplary right ear shade and the longitudinal axis of the exemplary left ear shade shown in the Figures. For example, the ear shades may be spaced closer or farther apart from one other and/or at different angles, as exemplified by the difference in spacing between the exemplary embodiment of FIG. 9 and the exemplary implementation of FIGS. 12A-12M.

As shown in FIGS. 1-9, in the exemplary embodiment, a shading portion 14 of a temple arm 10 is operatively connected to an ear support portion 12 and cooperates with the ear support portion to create a downward-opening cavity 16 into which the entire top of a user's ear extends to shade at least a top of the user's ear. In the exemplary embodiment shown, the shading portion 14 comprises a closed front portion 18, a top portion 20, and a side wall 22. As such, the cavity 16 is defined at least in part by the ear support portion 12, the closed front portion 18, the top portion 20, the side wall 22, and an open back 24. As shown in FIG. 6, the distance between the side wall 22 of the shading portion 14 and the ear support portion 12 of the temple arm 10 increases from the closed front portion 18 of the cavity 16 rearward to a point A, and then stays about the same distance apart from there rearward to the open back 24 of the cavity. Further, the size and shape of the exemplary temple arm 10 shown does not prohibit the user from wearing a hat, such as for example, a baseball cap or wide brimmed hat.

In this exemplary embodiment the side wall 22 of the shading portion 14 does not cover the entire ear of the user. As such, the side wall 22 does not prohibit the use of many electronic devices, such as for example, an ear bud, Bluetooth device, or phone, or perhaps even certain headphones. The shading portion 14 of the temple arm 10 also leaves the opening to the ear canal exposed, and thus does not prohibit the user from wearing and adjusting an in-canal hearing aid or other similar device. However, in alternate embodiments of the invention (not shown), the side wall of the shading portion may extend downward far enough to cover the ear canal opening or down far enough to cover the entire ear. Further, in other alternate embodiments of the invention (not shown), at least part of the shading portion 14 may comprise an expressive element, such as a structure shaped like a circle, square, oval, sports ball, fish, bike, or other shapes known in the art. At least part of the shading portion 14 may also comprise reflective material. For example, at least the outside surfaces of the shade potion exposed to sunlight may be covered with a reflective material (e.g., a reflective coating or overwrap) to help reduce heating by the sun.

Further, in the embodiment shown in FIGS. 1-9, a split 26 in the temple arm 10 at least in part defines the cavity 16. The anterior end 28 of the temple arm 10 comprises a top surface 30, an outer surface 32, and an inner surface 34. At the split 26, the outer surface 32 of the temple arm 10 forms the outer surface of the side wall 22 and the inner surface 34 of the temple arm forms the outer surface (surface towards the user's head) of the ear support portion 12. In the exemplary embodiment shown, the top surface 30 of the temple arm 10 is contiguous from the anterior end 28 to the posterior end 36 of the temple arm. The top surface 30 of the temple arm 10 widens at the split 26 to include the outer surface of the top portion 20 of the shading portion 14.

In the embodiment shown in FIGS. 1-9, the walls of the shading portion 14 are generally uniform in shape, so the inside shape of the cavity 16 generally follows the outside shape shown and the inside wall surfaces shown generally follow the outside wall surfaces shown. In this embodiment, the inner surface of the top portion 20 of the shading portion 14, beginning at the closed front portion 18, comprises a first convex portion 38 transitioning to a first concave portion 40 transitioning to a second concave portion 42 transitioning to a second convex portion 44 adjacent the open back 24 of the cavity 16. The second convex portion 44 permits the temple arm 10 to be pulled forward without catching on the ear when a user removes the glasses by allowing the open back 24 of the cavity to extend substantially horizontally.

The open back 24 of the temple arm 10 depicted in FIGS. 1-9 is above a bottom of the anterior end 28 of the temple arm when the ear support portion 12 of the temple arm is resting on the ear. The open back 24 permits the temple arm 10 to be pulled forward without catching on the ear when a user removes the glasses. The open back 24 and the length of the cavity 16 provide for a virtually universal fit (i.e., "one size fits all"). Further, as shown in FIG. 7, the posterior end 36 of the ear support portion 12 is visible from a front side of the temple arm 10.

As shown in FIGS. 1-9, the temple arm 10 further comprises an optional cavity 46 between the anterior end 28 of the temple arm 10 and the shading portion 14 of the temple arm. The cavity 46 may contain a material having a buoyancy that is higher than the material used to form the temple arm 10 so that the temple arm 10 floats and glasses with the temple arm float in water. Further, the cavity 46 may contain material having a padded and/or gripping surface contacting the temple of the user. The interior of the downward-opening cavity 16 and/or the bottom of the ear support portion 12 may also include a material having a padded and/or gripping surface contacting the ear of the user. The material may be attached to the temple arm 10 by any suitable method known in the art, such as for example, with an adhesive, fastener, or be overmolded on or otherwise molded to the temple arm.

As shown in FIGS. 1-9, the temple arm 10 optionally comprises at least one tether hole 48 at the posterior end 36, or tip, of the temple arm. The at least one tether hole 48 may be used to attach the temple arm 10 to a tether, such as a strap or string, for holding or storing the glasses. For example, a strap may attach to the posterior ends 36 of two temple arms 10 such that the glasses may hang around the user's neck. As shown, the posterior end 36, or tip, of the temple arm 10 is shaped to wrap around, or grip, the user's head. This configuration permits a substantial portion of the user's head and neck directly behind the ear to be shaded from sunlight that would otherwise be striking that region but for the use of the shades.

Figure 11A:
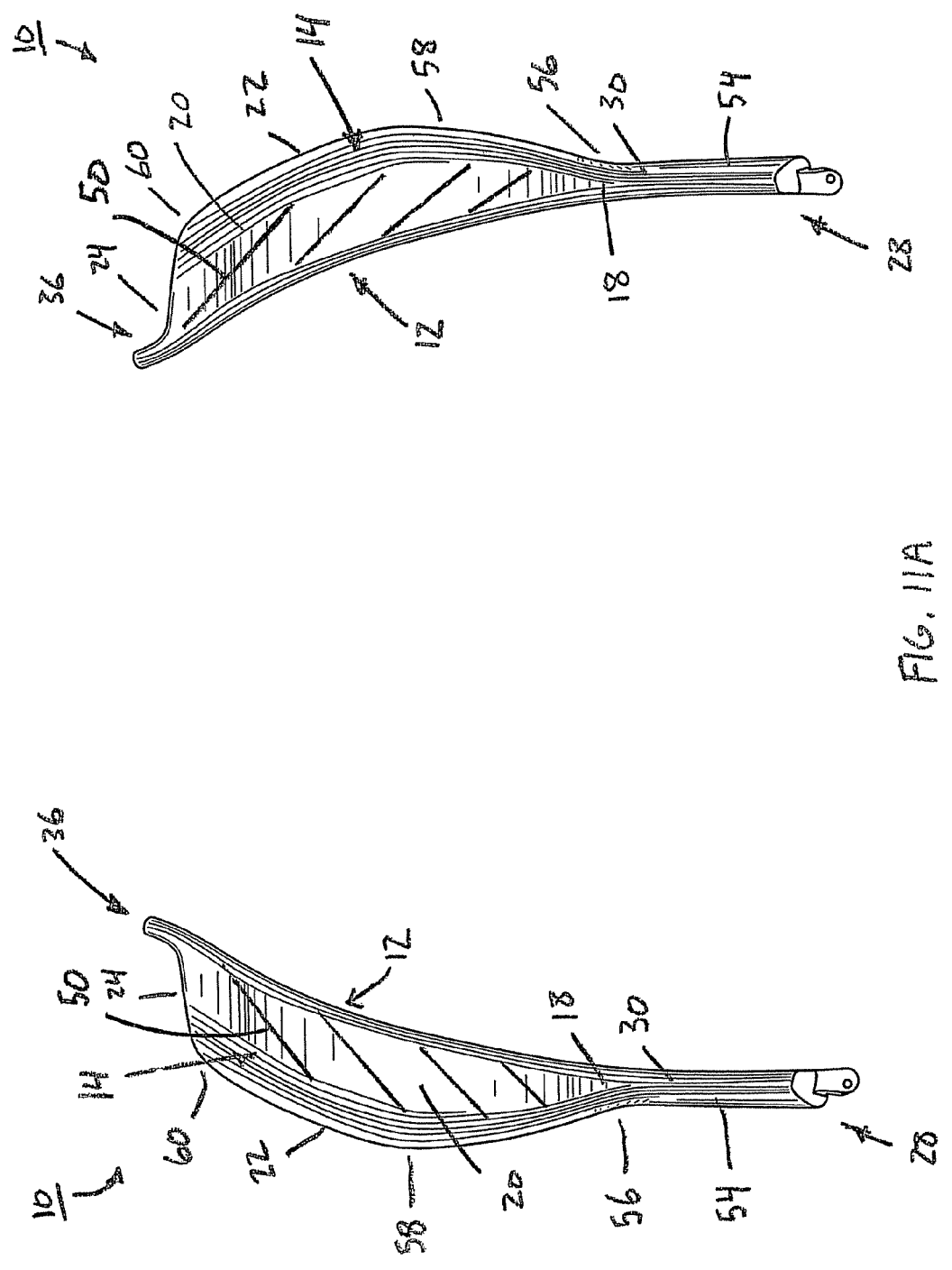
Figure 11B:
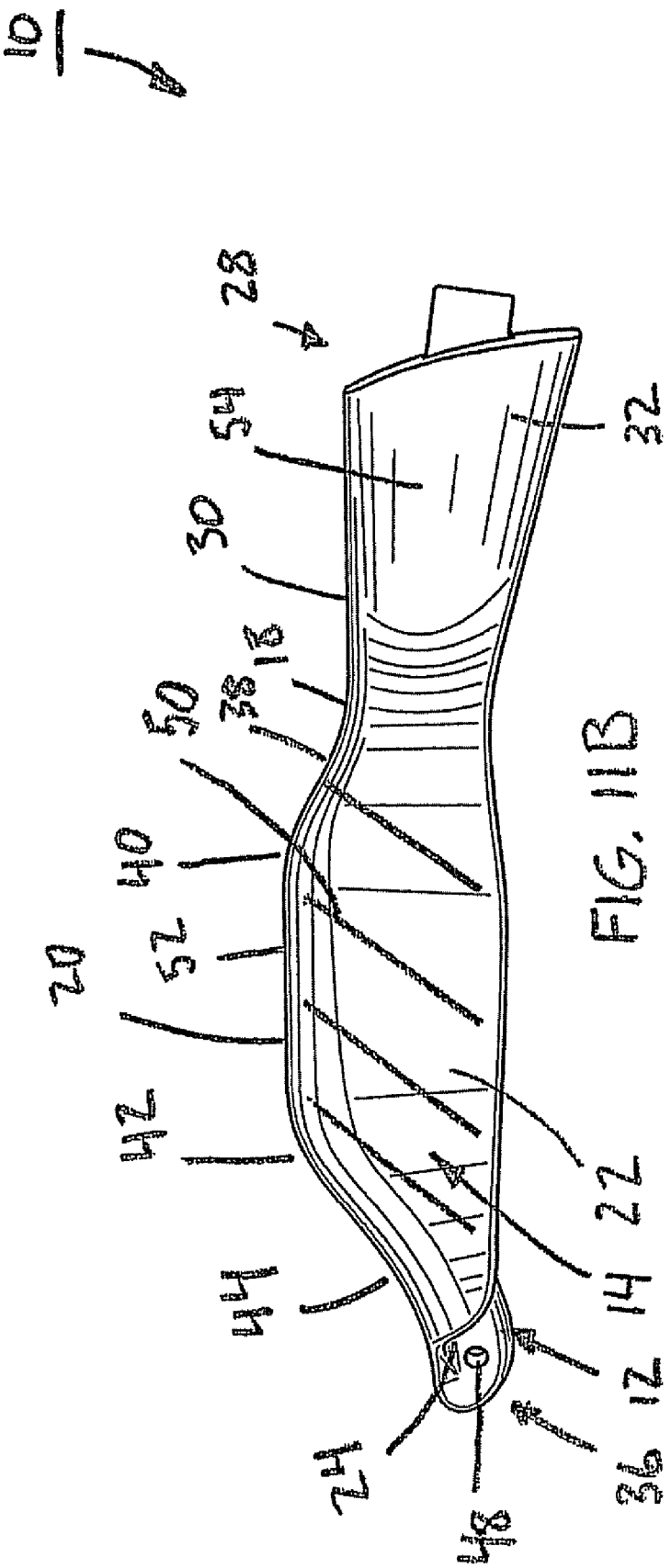
Figure 12A:
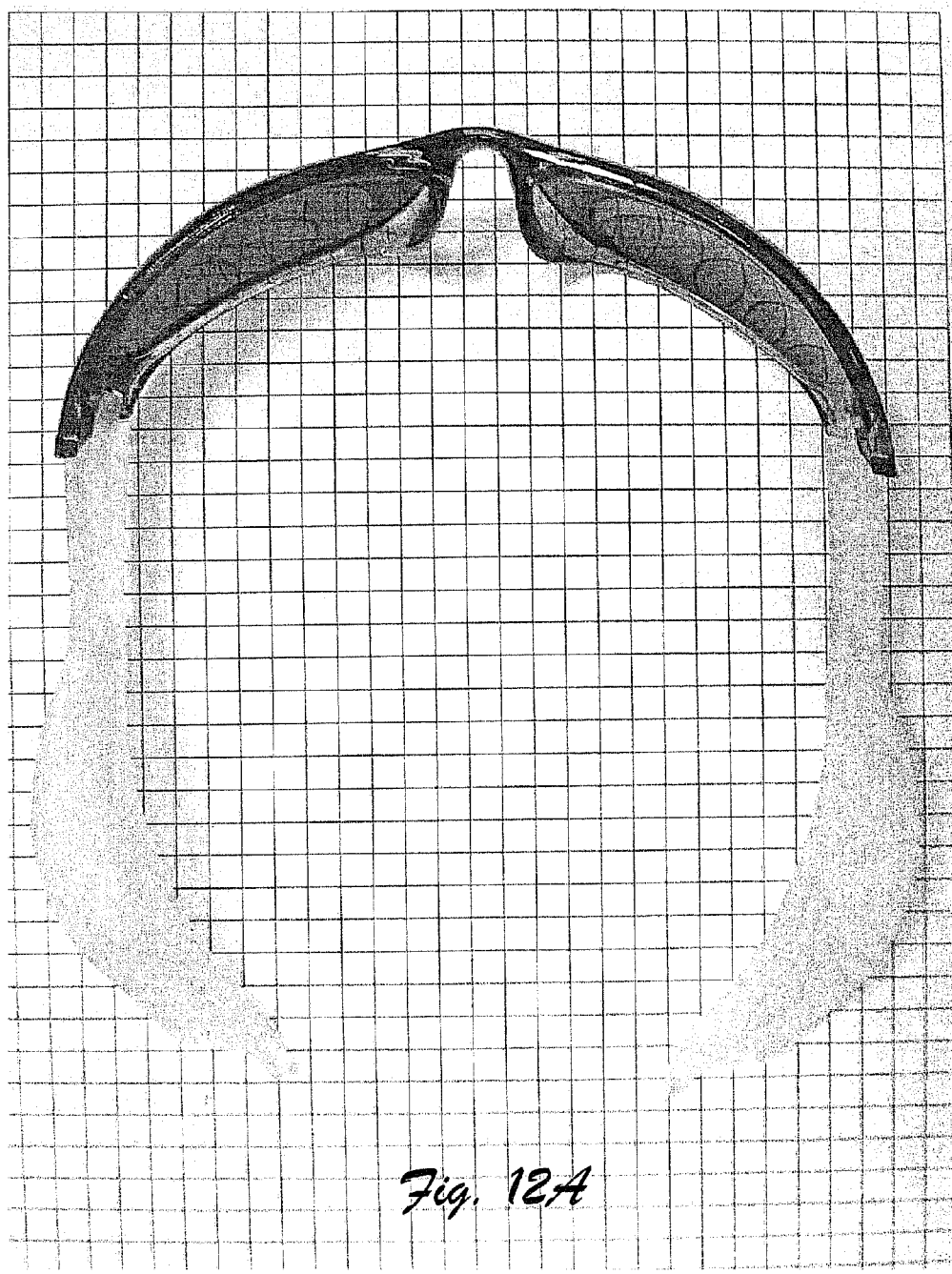
Figure 12B:
Figure 12C:
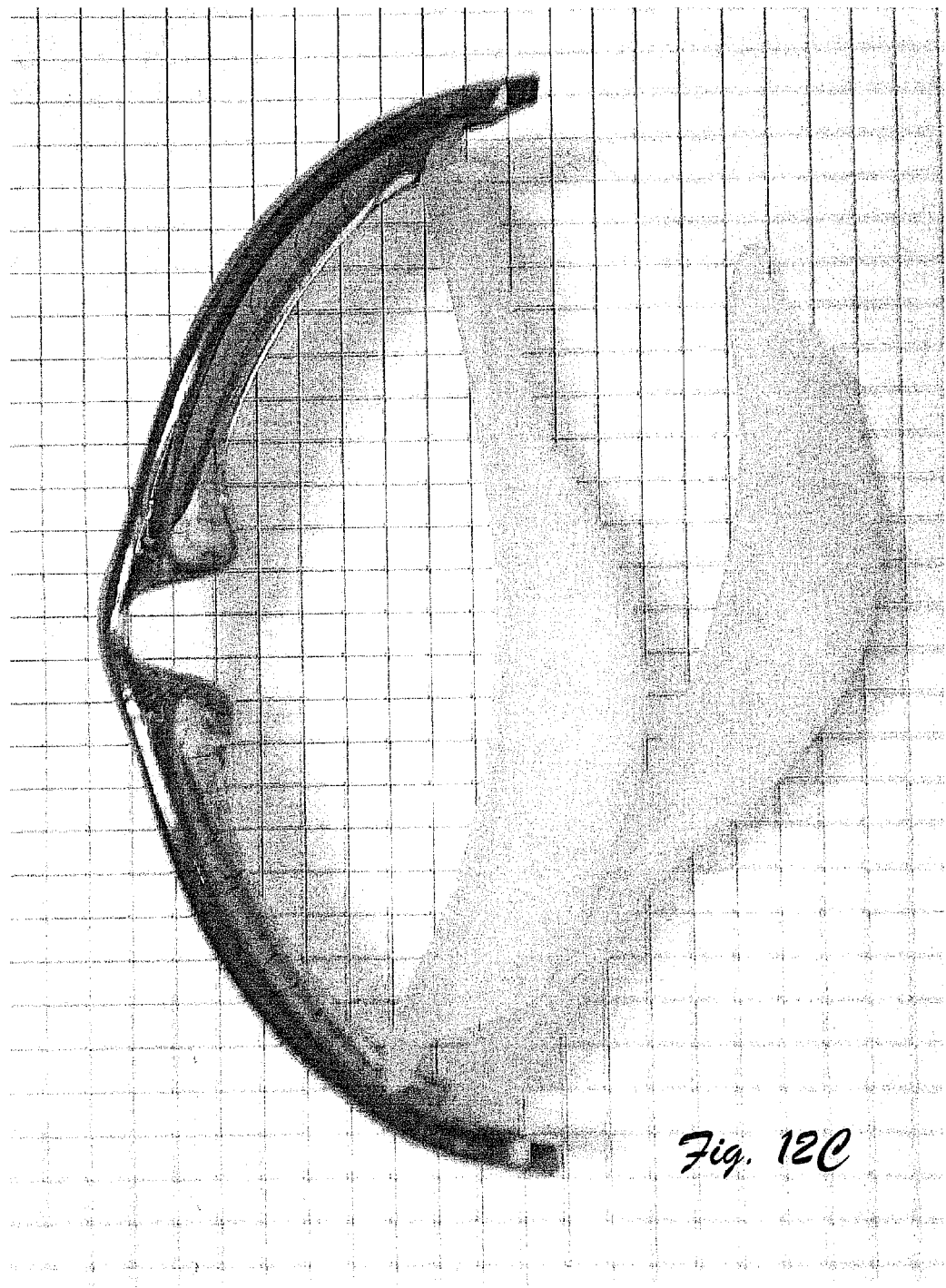
Figure 12D:
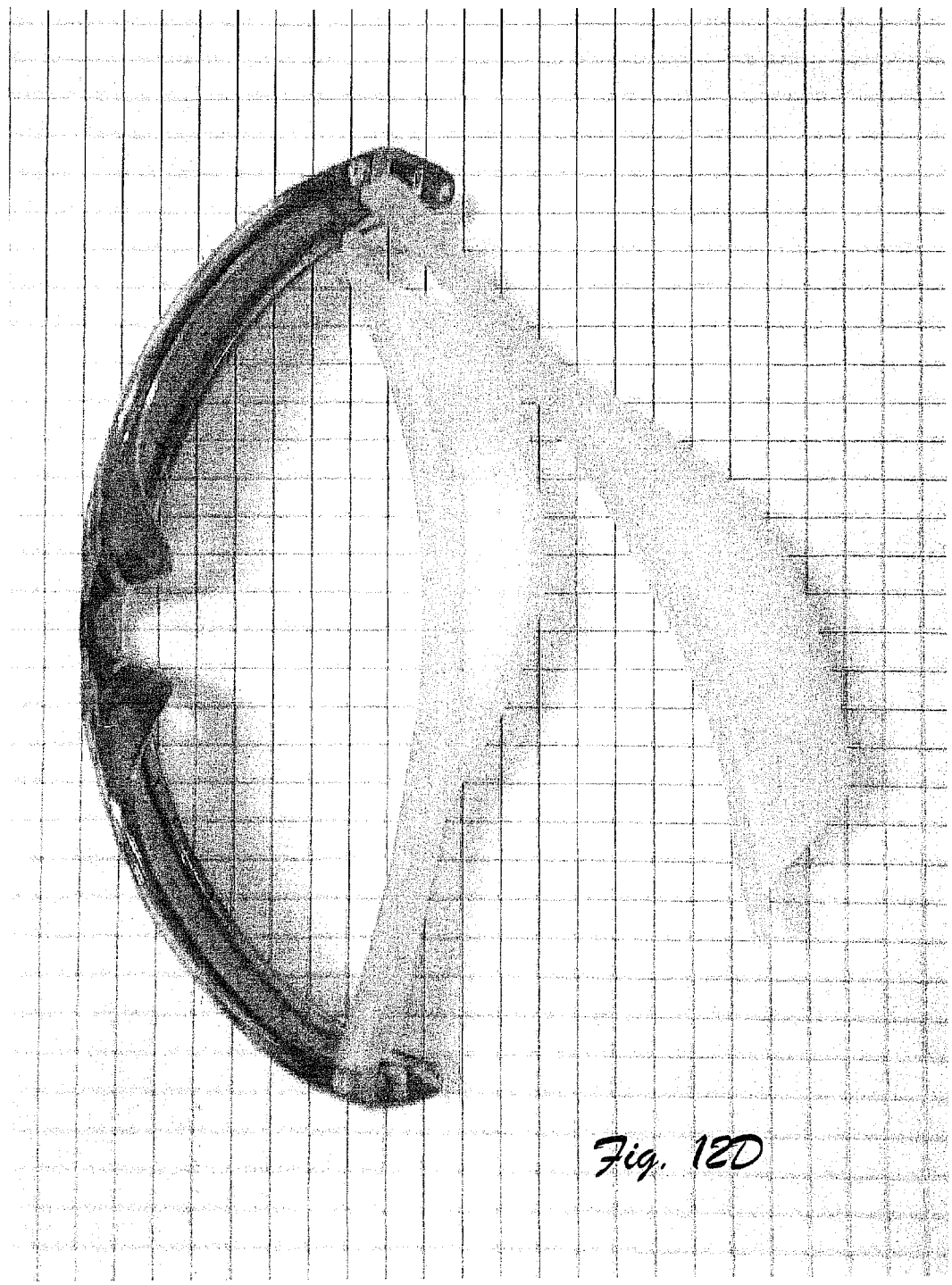
Figure 12E:
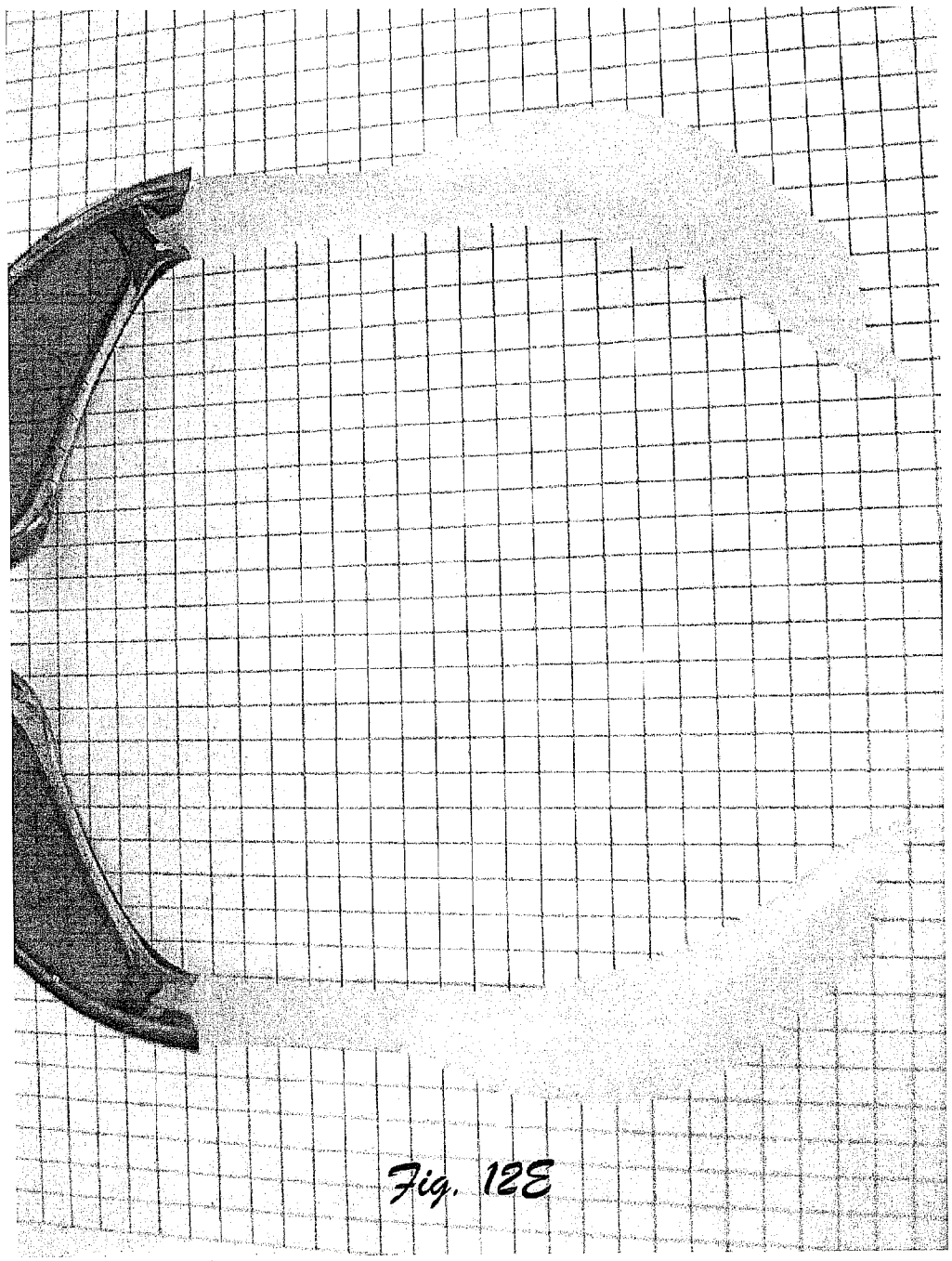
Figure 127:
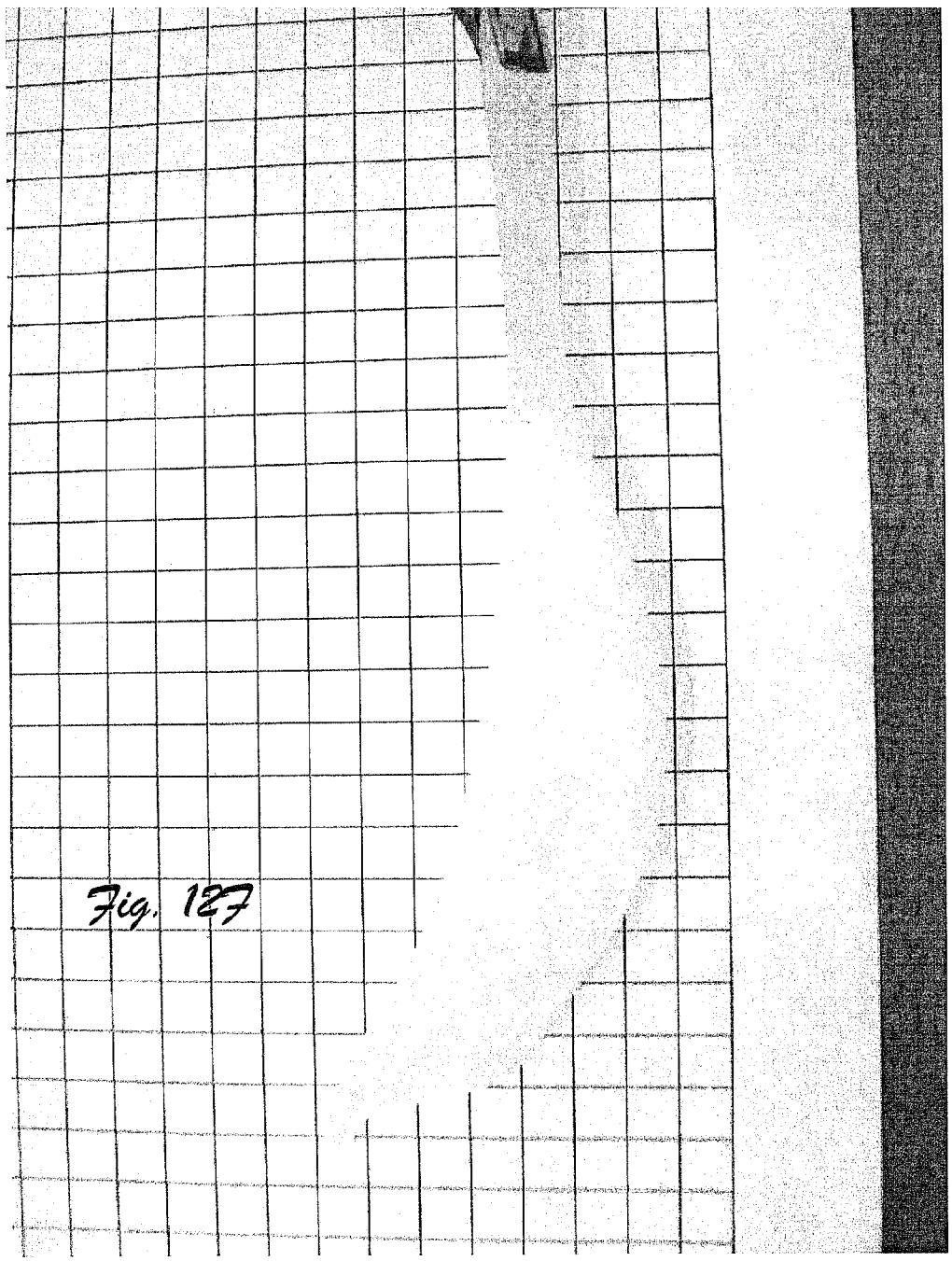
Figure 12G:
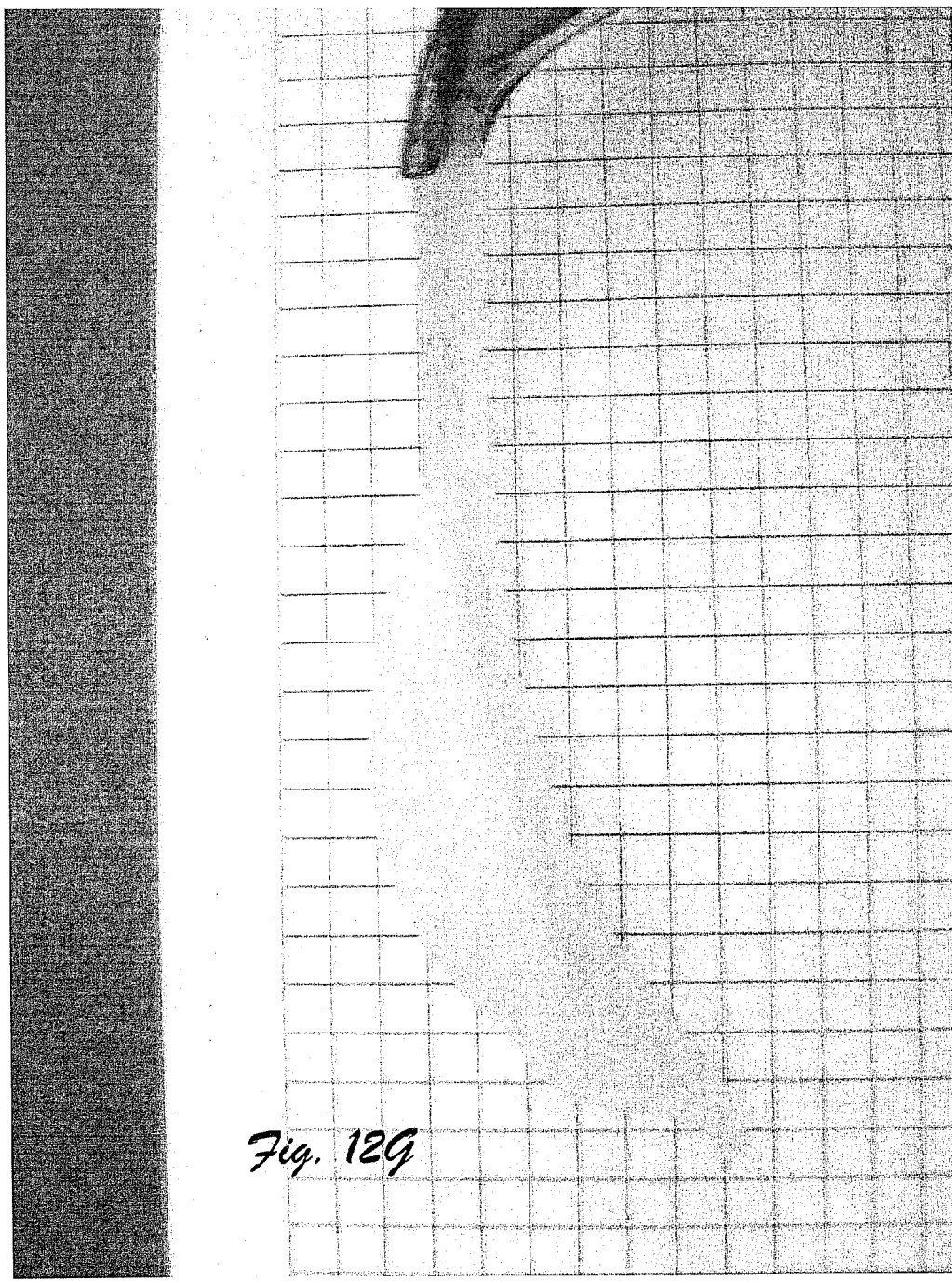
Figure 12H:
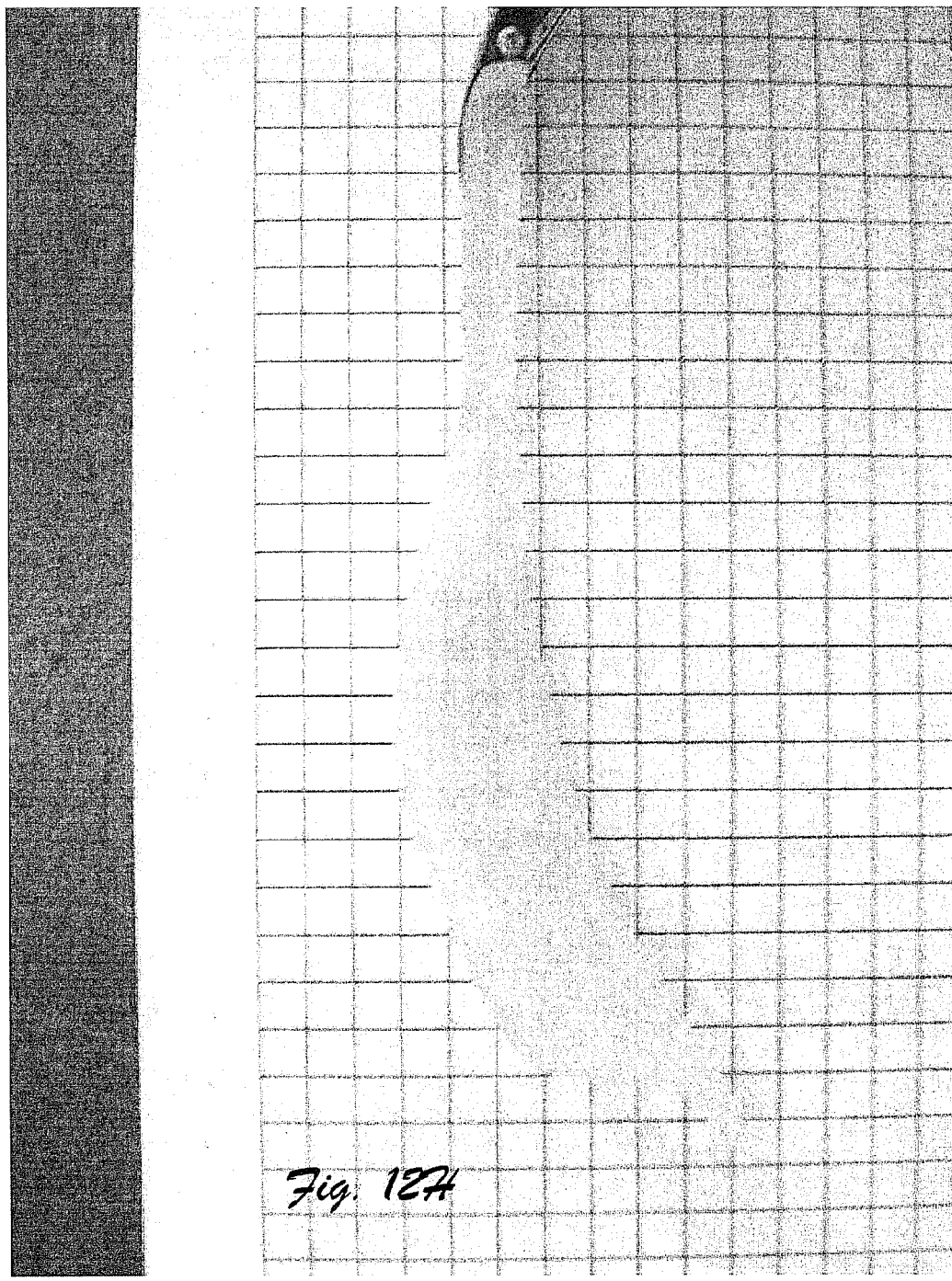
Figure 127:
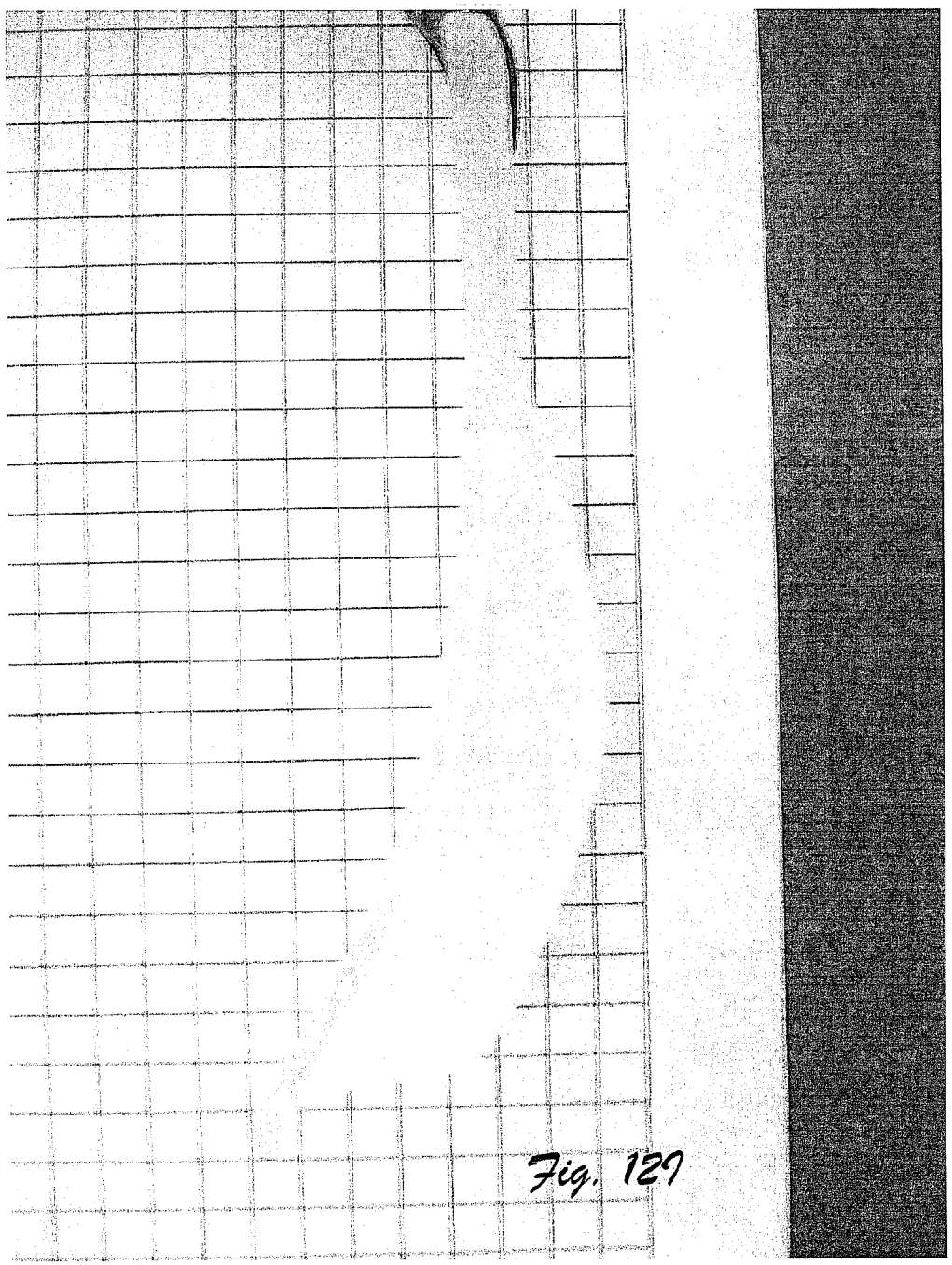
Figure 12J:
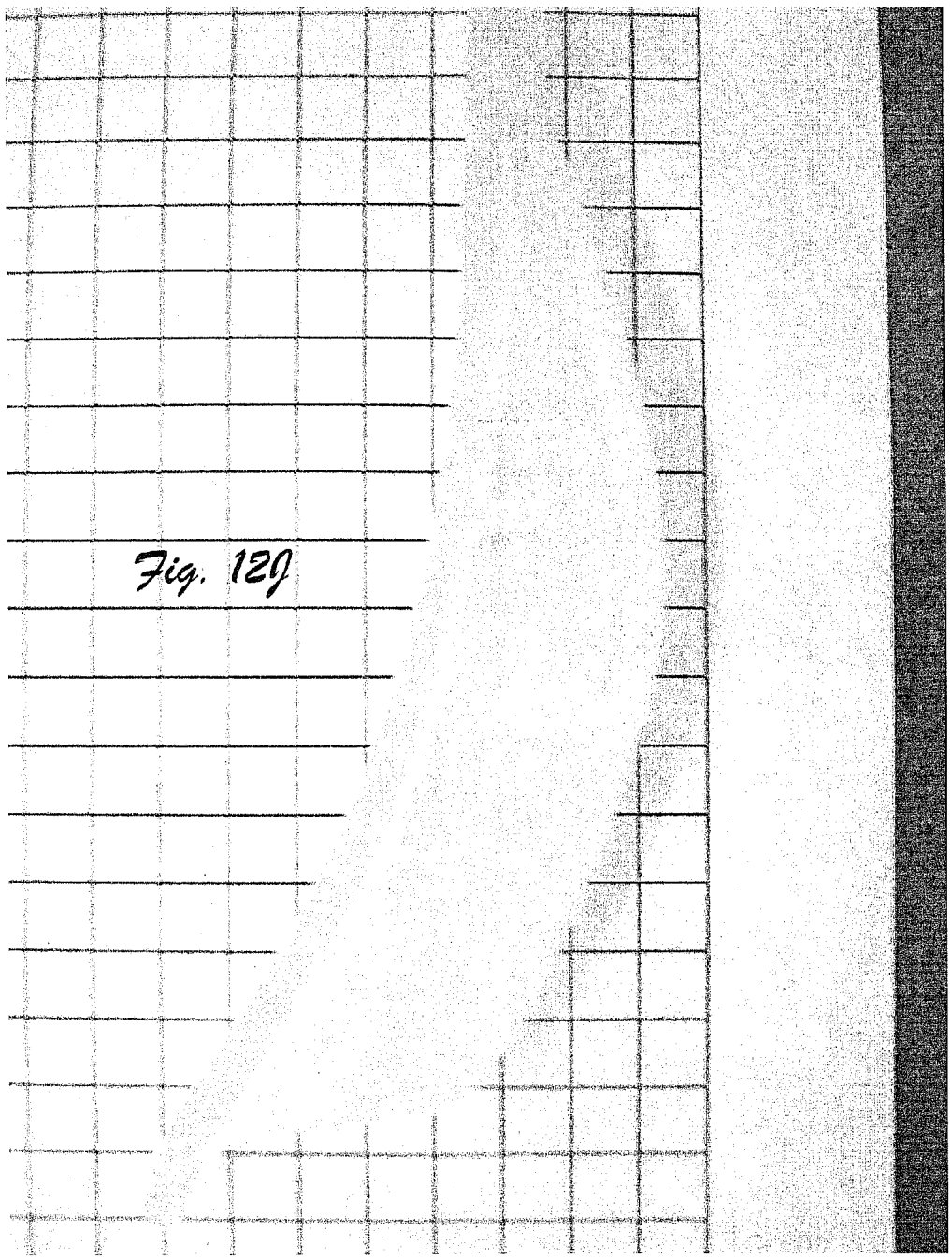
Figure 12K:
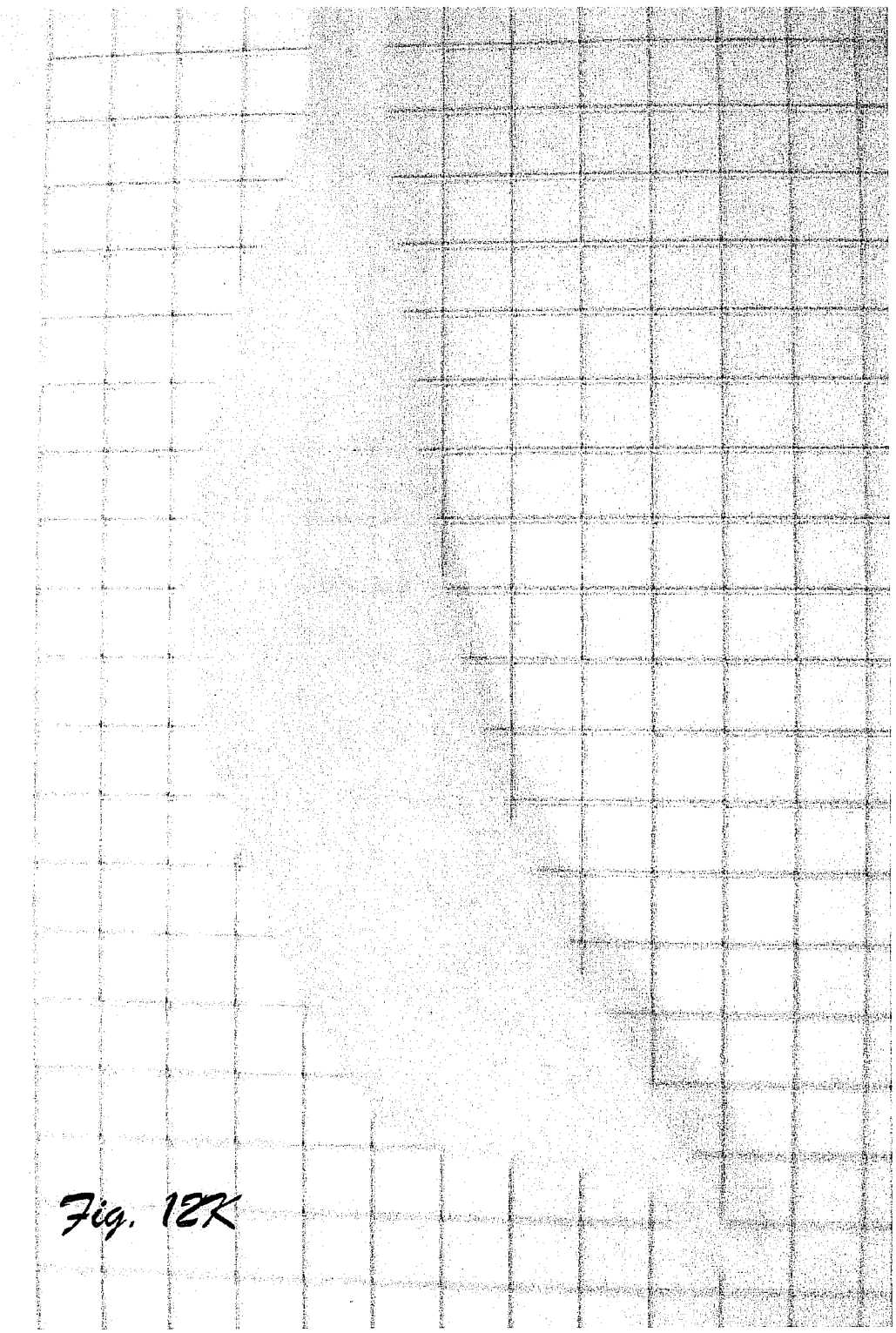
Figure 12L:
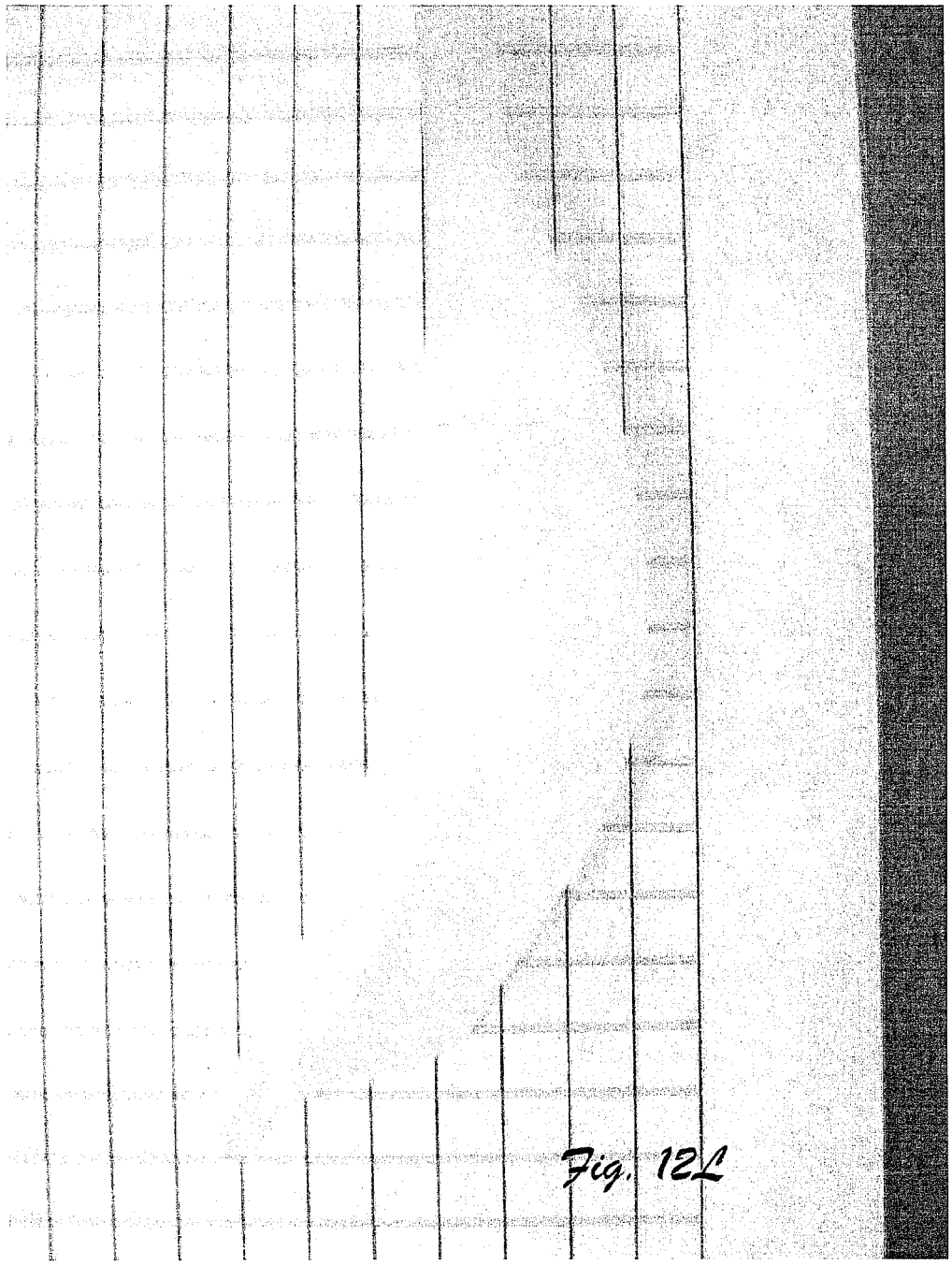
Figure 12M:
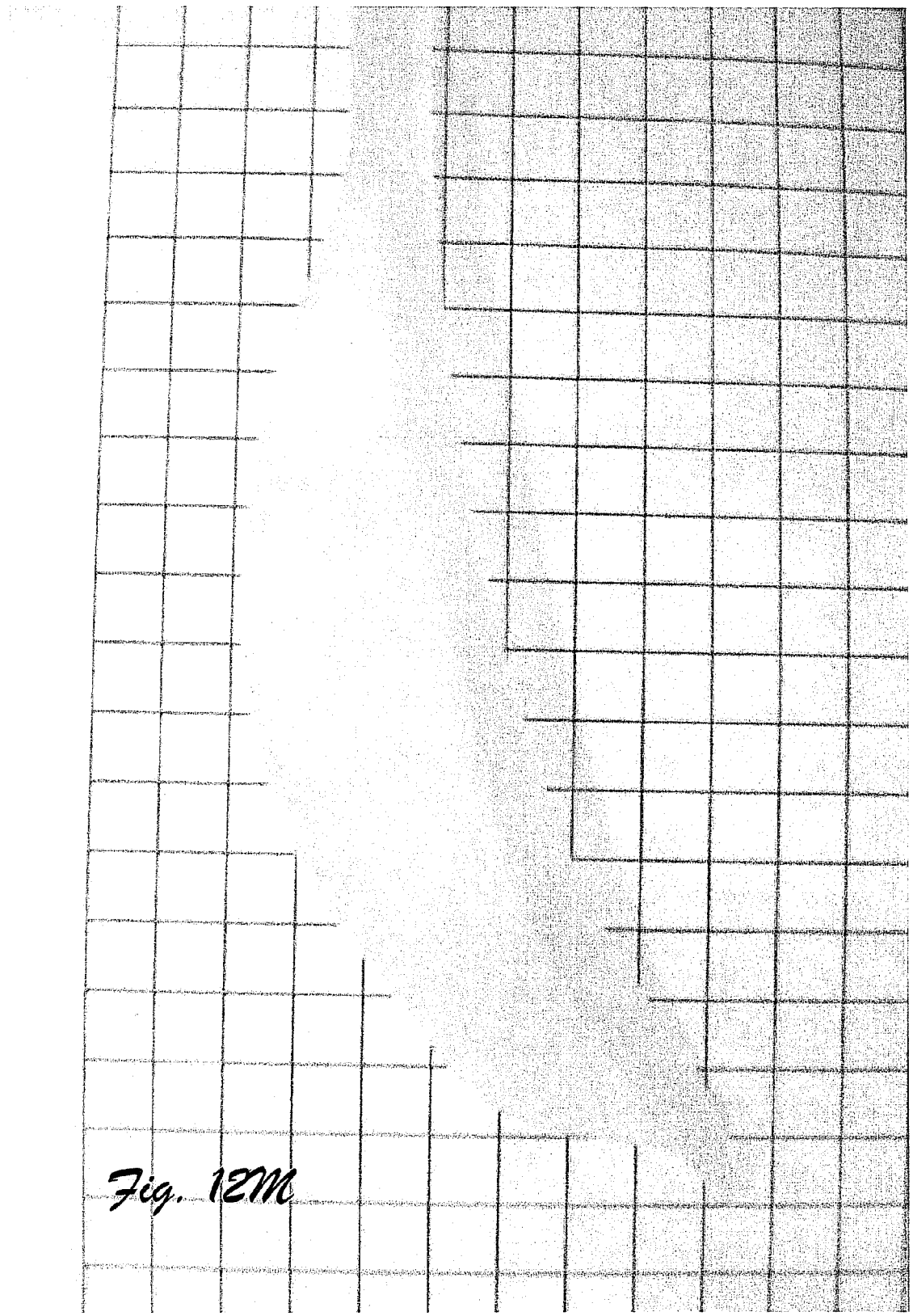

As shown in FIGS. 1-9, the top portion 20 and side wall 22 of the shading portion 14 are solid without any openings therein. However, in some embodiments (FIGS. 11A-11B), at least one of the top portion 20 and the side wall 22 has vent openings 50 therein, such as for example, small holes or narrow slits having a diameter or width of about 0.02 to 0.1 inches, about 0.03 to 0.09 inches, about 0.05 to 0.07 inches, about 0.060 to 0.065 inches, or about 0.062 inches. The vent openings 50 may be any suitable shape and size known in the art capable of ventilating the ear. Further, the vent openings 50 may be generally sized and shaped such that the shading portion 14 of the temple arm 10 still shades a substantial portion of the ear.

As shown in FIGS. 1-9, the top shade portion 20 of the temple arm 10 comprises a first downward-facing convex surface 38 transitioning to a first downward-facing concave surface 40 transitioning to a second downward-facing concave surface 42 transitioning to a second downward-facing convex surface 44 at the posterior end 36 of the top shade portion 20. A substantially flat portion 52 exists between the first downward-facing concave surface 40 and the second downward-facing concave surface 42.

As shown, the posterior end 36 of the top shade portion 20 is not curved downward thereby permitting the glasses to be removed from the user by merely pulling forward. Further, the posterior end 36 of the top shade portion 20 does not extend lower than a portion of the outside shade portion 22 vertically aligned with the center of the user's ear. The posterior end 36 of the top shade portion 20 exposes a central rear edge of the user's ear to light coming in horizontally from directly behind the user. In this embodiment, the posterior end 36 of the top shade portion 20 extends past the rear-most point of the user's ear to shade a central rear edge of the user's ear from light coming in at a 45 degree angle with respect to horizontal directly behind the user. In various embodiments (not shown), the posterior end of the top shade portion extends at least 0.5 inches or 0.75 inches or 1.0 inches or 1.25 inches or 1.5 inches past the rear-most point of the user's ear (or past the rearmost concave internal surface in the cavity) to shade a central rear edge of the user's ear from light coming in at a 45 degree angle with respect to horizontal directly behind the user.

The outer surface of the top shade portion 20 extends from the temple bar 54 posteriorly at least to an upward-facing convex surface 42 transitioning to an upward-facing concave surface 44 at the posterior end of the top shade portion.

The outside shade portion 22 of the temple arm 10 shown in FIGS. 1-9 extends down substantially vertically from the top shade portion 20. As shown in FIG. 5, the outer surface of the outside shade portion 22 extends from the temple bar 54 posteriorly to a first concave portion 56 transitioning to a first convex portion 58 transitioning to a second convex portion 60 at the posterior end 36 of the outside shade portion. In the exemplary embodiment shown, the ear canal opening of the ear is left exposed and uncovered by the outside shade portion, and in other embodiments (not shown) they may cover more of the ear or all of the ear, and may cover the ear canal opening. Further, at least the posterior ends 36 of the top shade portion 20 and the outside shade portion 22 form an open channel.

The temple bar 54 of the temple arm 10 shown in FIGS. 1-9 splits into an inside side portion and the outside shade portion 22. The inside side portion extends posteriorly to form the ear support portion 12 to support the glasses on the user's ear. The top shade portion 20 extends posteriorly between the inside side portion and the outside shade portion 22 to shade the front top edge of the user's ear, the top central edge of the user's ear, the rear top edge of the user's ear, the top front portion of the user's ear, the top central portion of the user's ear, and the top rear portion of the user's ear. The outside shade portion 22 and an inside side portion meet at a "V" 94 at the temple bar 54.

The temple arm 10 is sized and configured to leave the entire lower portion or lower third or lower half of the user's ear uncovered. The temple arm may be molded as an integral unit. Further, the temple bar may comprise a cavity. The cavity of the temple bar may contain a material having a buoyancy that is higher than the material used to form the temple bar so that the temple arm floats in water. The temple arm may include at least one tether hole.

Figure 9:
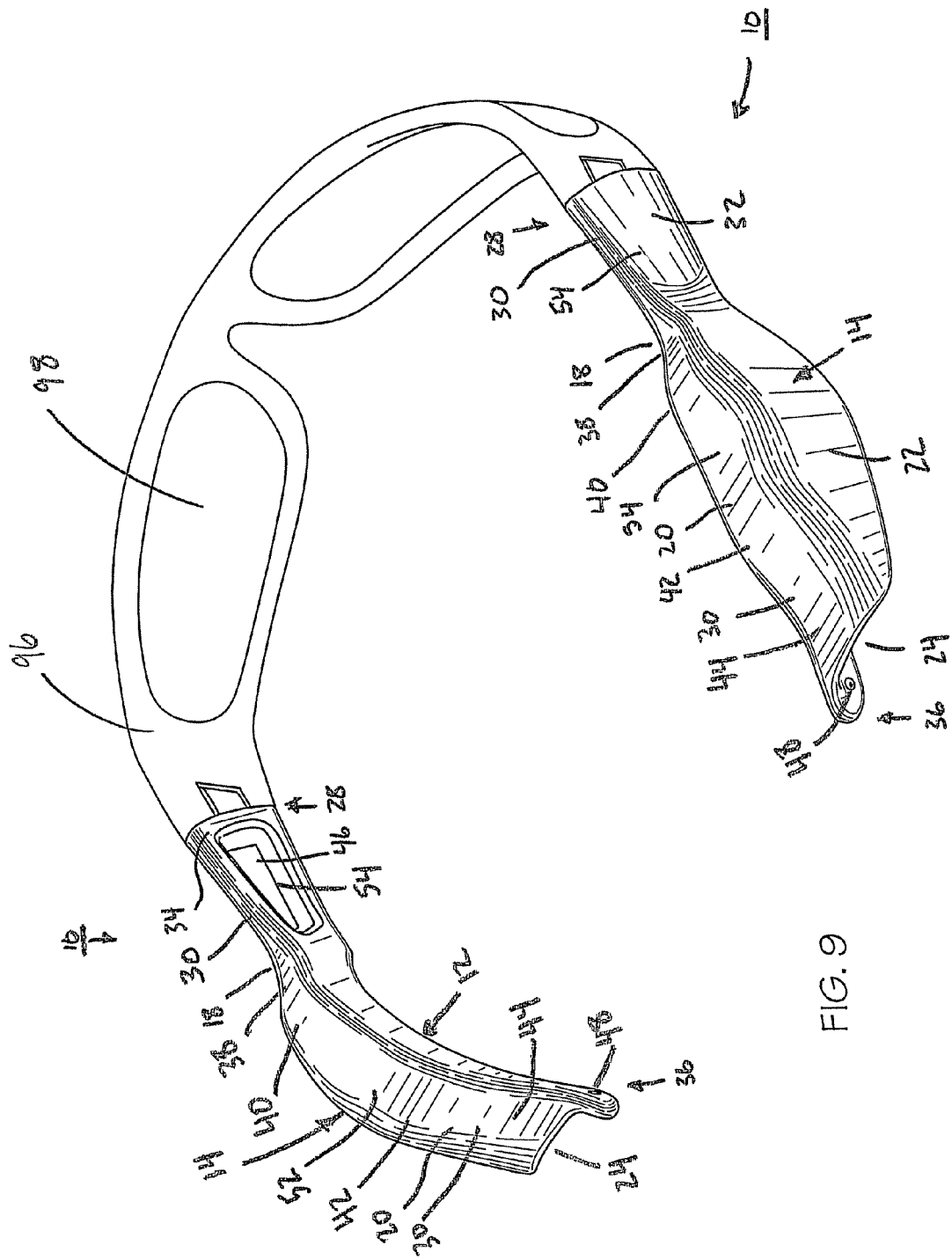
FIG. 9 is a rear/right/top perspective view thereof showing an exemplary lens portion.

As shown in FIG. 9, the anterior end 28 of each temple arm 10 is operatively connected to an exemplary lens holding portion 96 capable of holding two lenses 98. It should be noted, however, that virtually any pair of glasses having a lens holding portion and a pair of temple arms can be modified to take advantage of the various shade portions taught herein, e.g., either by manufacturing modified temple arms having the shade portions connected thereto, or by providing any of the shade portions taught herein to be operatively connected to the temple arms already connected to the lens holding portion (e.g., by adhesive or by a fastener such as a threaded fastener or via at least two holes in the shade portion through which the temple arm passes). Accordingly, virtually any other lens holding portions known in the art may be used in the practice of this invention, such as for example, various designs and models of glasses capable of holding one or more lenses. In other embodiments of the invention (not shown), the temple arm may be operatively connected to only a lens, in which case, the lens holding portion may be as simple as a hinge fastened to a lens. Further, as shown in FIG. 9, the anterior end 28 of each temple arm 10 is operatively connected to the lens holding portion 96 by a hinge. Each hinge comprises a pin connected at each end to the lens holding portion 96 and extending through a portion of the anterior end 28 of the temple, arm 10. The hinge allows the temple arm to pivot relative to the lens holding portion such that the glasses can be opened and closed. One attaches the temple arm 10 to the exemplary lens holding portion 96 by a threaded fastener, such as a screw.

Other exemplary embodiments include a temple arm comprising an anterior end and a posterior end, wherein the anterior end is capable of connecting to a front face of the glasses. Further, a rearward facing cavity that opens downward is defined by a split in the temple arm. The rearward facing cavity includes an open back at the posterior end of the temple arm, a closed front, an ear support portion that rests on the ear, and a shading portion that covers at least the top of the ear. The shading portion includes a side wall and a top wall. A convex portion of the top wall is located adjacent the open back and permits the temple arm to be pulled forward without catching on the ear when a user or removes the glasses by allowing the open back to open at least substantially horizontal. The open back is above a bottom of the anterior end of the temple arm when the ear support portion of the rearward facing cavity is resting on the ear.

In some exemplary embodiments, the temple arm comprises an anterior end, a posterior end, a top shade portion, an outside shade portion, and an ear support portion. The anterior end is configured to be operatively connected to a lens holding portion of the glasses. The temple bar is located at the anterior end of the temple arm. The top shade portion and the outside shade portion extend posteriorly from the temple bar and cooperate together to shade at least the front top edge of the user's ear, the top central edge of the user's ear, and the rear top edge of the user's ear. The outside shade portion extends downward from the top shade portion to shade at least the top front portion of the user's ear, the top central portion of the user's ear, and the top rear portion of the user's ear. The ear support portion extends downward from the top shade portion to form an ear support to support the glasses on the user's ear. The top shade portion and the outside shade portion are sized and configured to leave the bottom rear edge of the user's ear and the entire lower portion of the user's ear uncovered. In some embodiments, the top shade portion comprises a downward-facing concave surface transitioning to a downward-facing convex surface at the posterior end of the top shade portion to facilitate removal of the glasses by pulling forward.

Other exemplary embodiments of the invention include a pair of glasses for shading the ears from the sun. The pair of glasses generally comprises a frame front and two temple arms, each temple arm capable of shading the ear from the sun. Each temple arm may comprise, or consist of, any of the temple arm embodiments disclosed herein, perhaps modified as taught herein. Each temple arm may comprise an anterior end, a posterior end, a rearward facing cavity having an open back at the posterior end of the temple arm, a closed front, an ear support portion that rests on the ear, and a shading portion that covers at least the top of the ear. The anterior end of the temple arm may be capable of connecting to the frame front of the glasses. The rearward facing cavity may open downward. The open back of the rearward facing cavity may permit the temple arm to be pulled forward without catching on the ear when a user removes the glasses.

I claim:

1. A temple for glasses that when worn by a user are capable of shading at least a top portion of the user's ear from the sun, comprising:
   an anterior end and a posterior end, wherein the anterior end of the temple arm is configured to be operatively connected to a lens holding portion of the glasses;
   a temple bar at the anterior end;
   a top shade portion and an outside shade portion both extending posteriorly from the temple bar and cooperating together to shade at least the front top edge of the user's ear, the top central edge of the user's ear, and the rear top edge of the user's ear, with the outside shade portion extending downward from the top shade portion to shade at least the top front portion of the user's ear, the top central portion of the user's ear, and the top rear portion of the user's ear; and
   an ear support portion extending downward from the top shade portion to form an ear support to support the glasses on the user's ear; and
   wherein the top shade portion and the outside shade portion are sized and configured to leave the bottom rear edge of the user's ear and the entire lower portion of the user's ear uncovered.

2. The temple arm of claim 1, wherein the top shade portion comprises a downward-facing concave surface transitioning to a downward-facing convex surface at the posterior end of the top shade portion to facilitate removal of the glasses by pulling forward.

3. The temple arm of claim 1, wherein at least one of the top shade portion and the outside shade portion have vent openings therein.

4. The temple arm of claim 1, wherein the top shade portion and the outside shade portion are solid without any openings therein.

5. The temple arm of claim 1, wherein the outside shade portion extends down substantially vertically from the top shade portion.

6. The temple arm of claim 1, wherein the top shade portion comprises a first downward-facing convex surface transitioning to a first downward-facing concave surface transitioning to a second downward-facing concave surface transitioning to a second downward-facing convex surface at the posterior end of the top shade portion.

7. The temple arm of claim 6 wherein there is a substantially flat portion between the first downward-facing concave surface and the second downward-facing concave surface.

8. The temple arm of claim 1, wherein the temple bar splits into an inside side portion and the outside shade portion, the inside side portion extending posteriorly to form the ear support portion to support the glasses on the user's ear, and the top shade portion extending posteriorly between the inside side portion and the outside shade portion to shade the front top edge of the user's ear, the top central edge of the user's ear, the rear top edge of the user's ear, the top front portion of the user's ear, the top central portion of the user's ear, and the top rear portion of the user's ear.

9. The temple arm of claim 1, wherein (i) the posterior end of the top shade portion is not curved downward thereby permitting the glasses to be removed from the user by merely pulling forward, (ii) the posterior end of the top shade portion does not extend lower than a portion of the side shade portion vertically aligned with the center of the user's ear, (iii) the posterior end of the top shade portion exposes a central rear edge of the user's ear to light coming in horizontally from directly behind the user, and (iv) the posterior end of the top shade portion extends at least about 0.5 inches past the rearmost point of the user's ear to shade a central rear edge of the user's ear from light coming in at about a 45 degree angle with respect to horizontal directly behind the user.

10. The temple arm of claim 1, wherein the outside shade portion and an inside side portion meet at a "V" at the temple bar.

11. The temple arm of claim 1, wherein at least the posterior ends of the top shade portion and the outside shade portion form an open channel.

12. The temple arm of claim 1, wherein the outer surface of the top shade portion extends from the temple bar posteriorly at least to an upward-facing convex surface transitioning to an upward-facing concave surface at the posterior end of the top shade portion.

13. The temple arm of claim 1, wherein the ear canal opening is left exposed and uncovered by the outside shade portion.

14. The temple arm of claim 1, wherein the temple bar further comprises a cavity containing a material having a buoyancy that is higher than the material used to form the temple bar so that the temple arm floats in water.

15. The temple arm of claim 1, wherein the temple arm is sized and configured to leave the entire lower portion or lower third or lower half of the user's ear uncovered.

16. The temple arm of claim 1, wherein the temple arm is molded as an integral unit.

17. The temple arm of claim 1, wherein the outer surface of the outside shade portion extends from the temple bar posteriorly to a first concave portion transitioning to a first convex portion transitioning to a second convex portion at the posterior end of the outside shade portion.

18. The temple arm of claim 1, wherein an inner surface of the top shade portion includes a spacer to cushion the user's ear and protect the user's ear from resting against the potentially warm, top shade portion.

19. A pair of glasses for shading the ears from the sun, comprising:
a lens holding portion; and
two temple arms operatively connected to the lens holding portion, each temple arm comprising:
an anterior end and a posterior end, wherein the anterior end of the temple arm is configured to be operatively connected to the lens holding portion;
a temple bar at the anterior end;
a top shade portion and an outside shade portion both extending posteriorly from the temple bar and cooperating together to shade at least the front top edge of the user's ear, the top central edge of the user's ear, and the rear top edge of the user's ear, with the outside shade portion extending downward from the top shade portion to shade at least the top front portion of the user's ear, the top central portion of the user's ear, and the top rear portion of the user's ear; and
an ear support portion extending downward from the top shade portion to form an ear support to support the glasses on the user's ear; and
wherein the top shade portion and the outside shade portion are sized and configured to leave the bottom rear edge of the user's ear and the entire lower portion of the user's ear uncovered.

20. A temple arm for glasses that when worn by a user are capable of shading at least a top portion of the user's ear from the sun, comprising:
an anterior end and a posterior end, wherein the anterior end of the temple arm is configured to be operatively connected to a lens holding portion of the glasses;
a temple bar at the anterior end;
a top shade portion and an outside shade portion both extending posteriorly from the temple bar and cooperating together to shade at least the front top edge of the user's ear, the top central edge of the user's ear, and the rear top edge of the user's ear, with the outside shade portion extending downward from the top shade portion to shade at least the top front portion of the user's ear, the top central portion of the user's ear, and the top rear portion of the user's ear; and
an ear support portion extending downward from the top shade portion to form an ear support to support the glasses on the user's ear; and
wherein:
the top shade portion comprises a downward-facing concave surface transitioning to a downward-facing convex surface at the posterior end of the top shade portion to facilitate removal of the glasses by pulling forward; and
the outer surface of the top shade portion extends from the temple bar posteriorly at least to an upward-facing convex surface transitioning to an upward-facing concave surface at the posterior end of the top shade portion; and
the top shade portion and the outside shade portion are sized and configured to leave the bottom rear edge of the user's ear and the entire lower portion of the user's ear uncovered; and
the outside shade portion extends down substantially vertically from the top shade portion; and
the temple bar splits into an inside side portion and the outside shade portion, the inside side portion extending posteriorly to form the ear support portion to support the glasses on the user's ear, and the top shade portion extending posteriorly between the inside side portion and the outside shade portion; and
at least the posterior ends of the top shade portion and the outside shade portion form an open channel.

* * * * *

UNITED STATES PATENT AND TRADEMARK OFFICE
CERTIFICATE OF CORRECTION

| | | |
|---|---|---|
| PATENT NO. | : 8,197,061 B2 | Page 1 of 1 |
| APPLICATION NO. | : 12/999665 | |
| DATED | : June 12, 2012 | |
| INVENTOR(S) | : Daniel J. Kindl | |

It is certified that error appears in the above-identified patent and that said Letters Patent is hereby corrected as shown below:

In claim 19, column 9, line 59, after "temple" please delete "anus" and insert -- arms --.

Signed and Sealed this
Thirty-first Day of July, 2012

David J. Kappos
*Director of the United States Patent and Trademark Office*